(12) United States Patent
Zetter et al.

(10) Patent No.: US 9,687,467 B2
(45) Date of Patent: Jun. 27, 2017

(54) DIAGNOSIS AND TREATMENT OF TAXANE-RESISTANT CANCERS

(75) Inventors: Bruce R. Zetter, Wayland, MA (US); Amy Holleman, Woudenberg (NL); Ivy Chung, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 42 days.

(21) Appl. No.: 14/009,686

(22) PCT Filed: Apr. 4, 2012

(86) PCT No.: PCT/US2012/032067
§ 371 (c)(1),
(2), (4) Date: May 28, 2014

(87) PCT Pub. No.: WO2012/138691
PCT Pub. Date: Oct. 11, 2012

(65) Prior Publication Data
US 2014/0329879 A1 Nov. 6, 2014

Related U.S. Application Data

(60) Provisional application No. 61/471,565, filed on Apr. 4, 2011.

(51) Int. Cl.
| | | |
|---|---|---|
| *C12N 15/11* | (2006.01) | |
| *A61K 31/337* | (2006.01) | |
| *A61K 45/06* | (2006.01) | |
| *A61K 31/7088* | (2006.01) | |
| *C12Q 1/68* | (2006.01) | |

(52) U.S. Cl.
CPC ........ *A61K 31/337* (2013.01); *A61K 31/7088* (2013.01); *A61K 45/06* (2013.01); *C12Q 1/6886* (2013.01); *C12Q 2600/106* (2013.01); *C12Q 2600/112* (2013.01)

(58) Field of Classification Search
CPC .................................................. A61K 31/337
See application file for complete search history.

(56) References Cited

U.S. PATENT DOCUMENTS 8,445,198 B2 * 5/2013 Knudsen ........................ 435/6.1
2003/0219768 A1 11/2003 Beebe et al.

FOREIGN PATENT DOCUMENTS

WO    WO 2009-157204 A1    12/2009
WO    WO 2010/027513 A2    3/2010

OTHER PUBLICATIONS

Navarro et al. Blood 2009, 114:2945-2951.*
microRNA.org—targets and expression, retrieved on Nov. 23, 2015 from www.microrna.org/microrna/releaseNotes.do#GeneralInformation, pp. 1-6.*
Wu et al. Cancer Biology & Therapy 13:5, 281-288.*
Kutanzi et al. Clin. Epigenet 2: 171-185, 2011.*
International Search Report and Written Opinion for PCT/US12/032067 mailed Nov. 23, 2012.
International Preliminary Report on Patentability for PCT/US12/032067 mailed Oct. 17, 2013.
Holleman et al., miR-135a contributes to paclitaxel resistance in tumor cells both in vitro and in vivo. Oncogene. Oct. 27, 2011;30(43):4386-98. Epub May 9, 2011.

* cited by examiner

*Primary Examiner* — Brian Whiteman
(74) *Attorney, Agent, or Firm* — Wolf, Greenfield & Sacks, P.C.

(57) ABSTRACT

Provided herein are methods and assays relating to the diagnosis and treatment of a taxane-resistant cancer. Such methods and assays comprise determining the level of expression of miR-135a in a biological sample from a subject having or suspected of having a taxane-resistant cancer or from a subject that was or is being treated with a taxane anti-cancer agent. Also provided herein are methods for treating such cancers by administering an inhibitor of the miR-135a pathway and a taxane to a subject in need thereof.

14 Claims, 24 Drawing Sheets

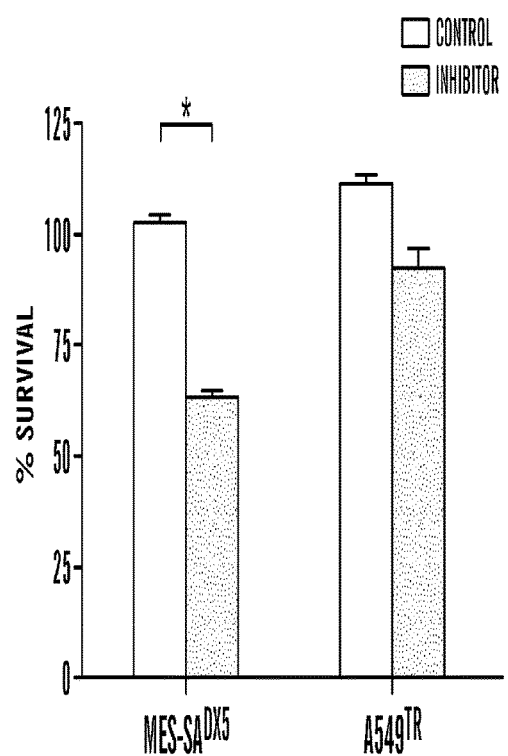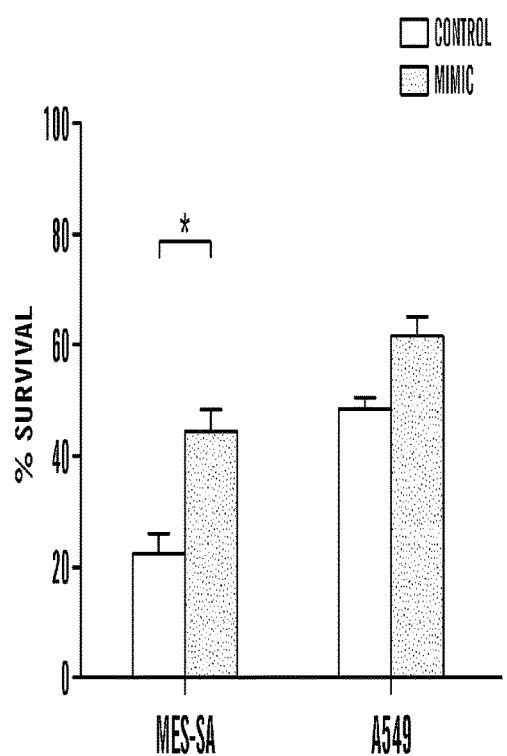
*FIG. 2A*  *FIG. 2B*

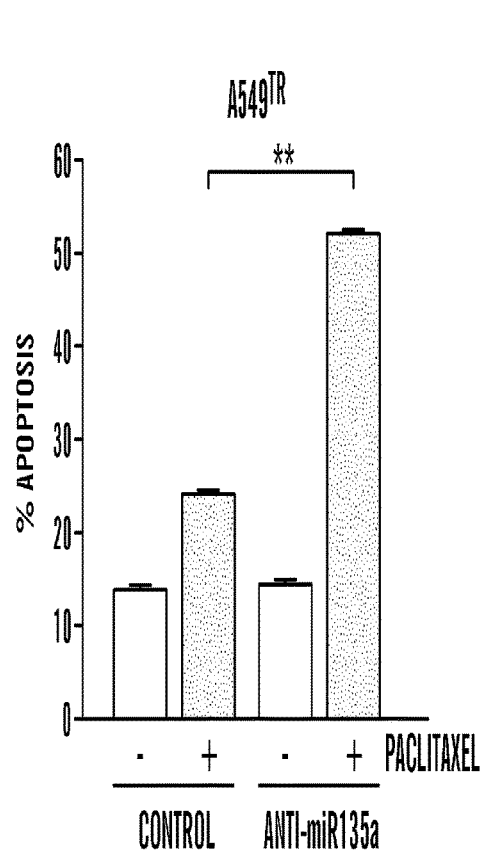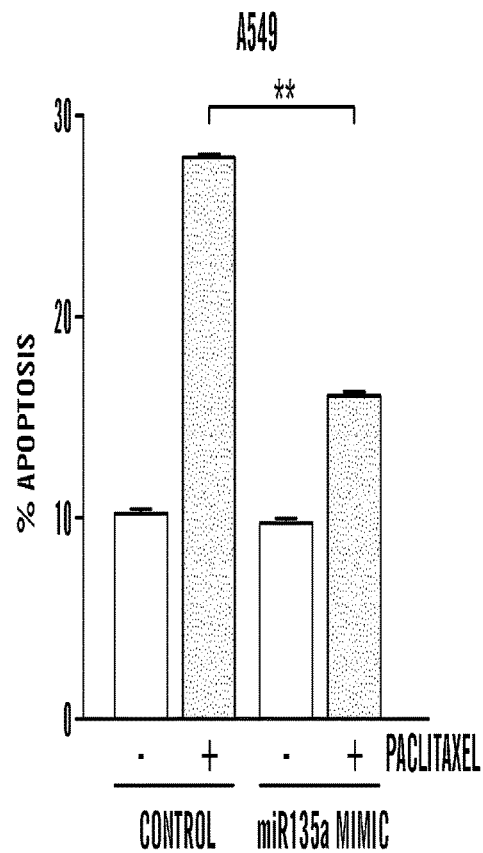
*FIG. 2C*  *FIG. 2D*

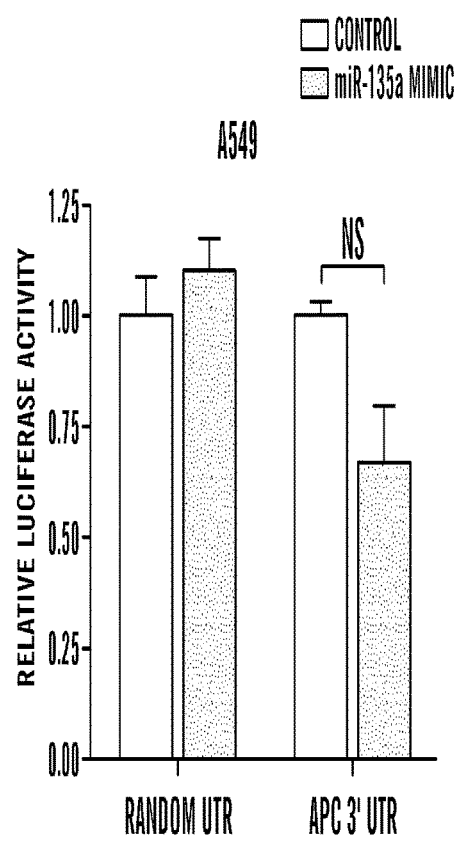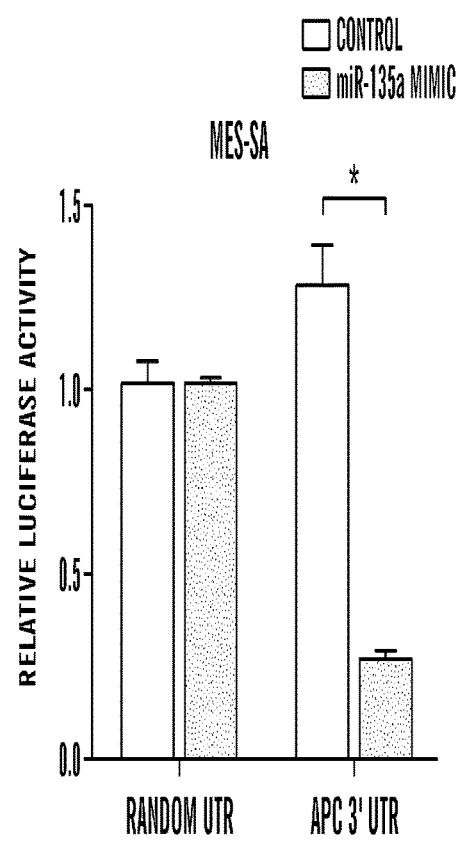
*FIG. 3A*  *FIG. 3B*

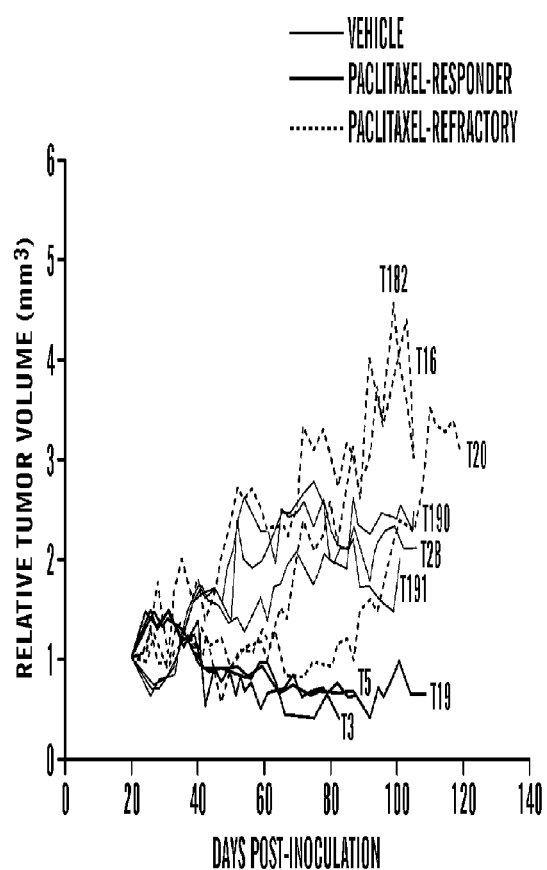
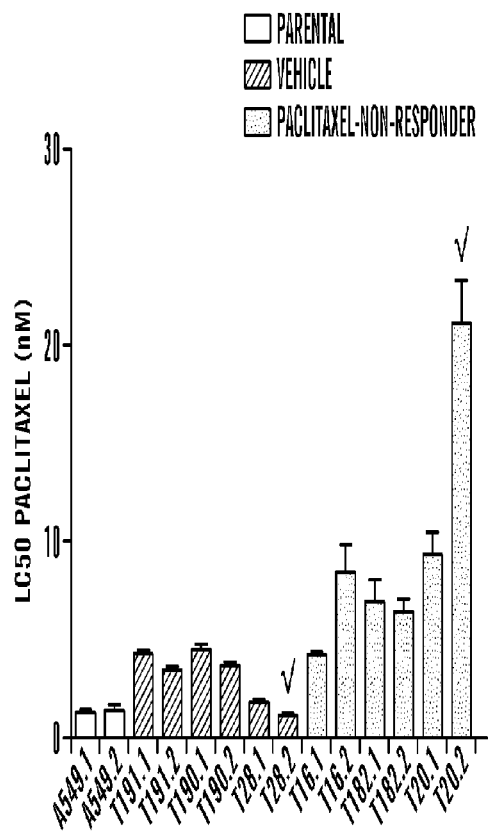
FIG. 5B
FIG. 5C

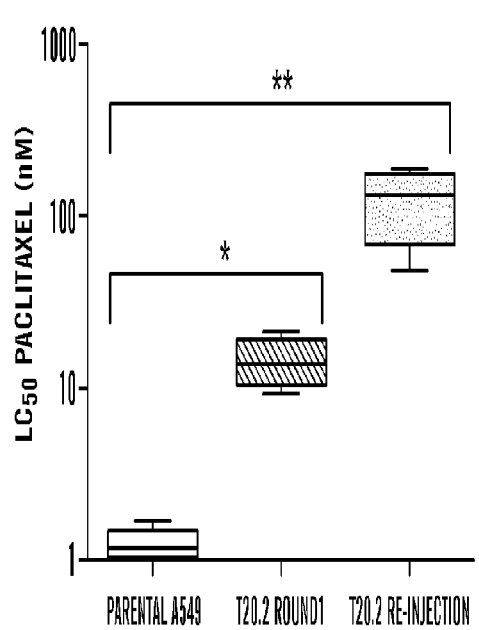 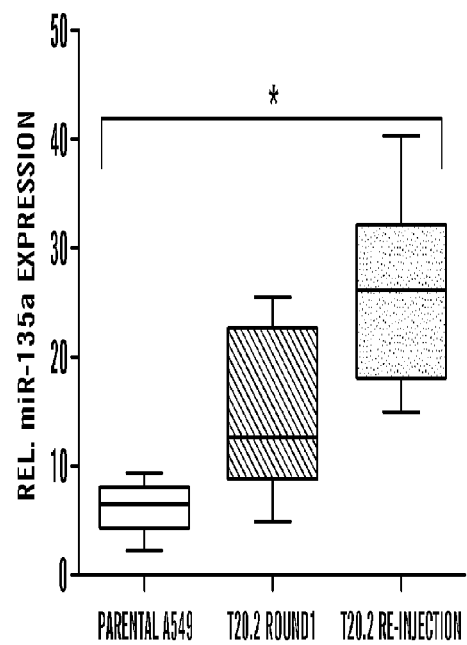
*FIG. 7A*  *FIG. 7B*

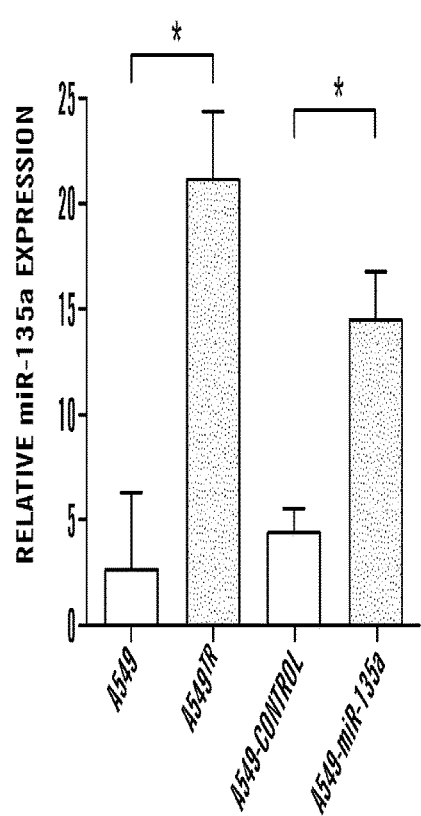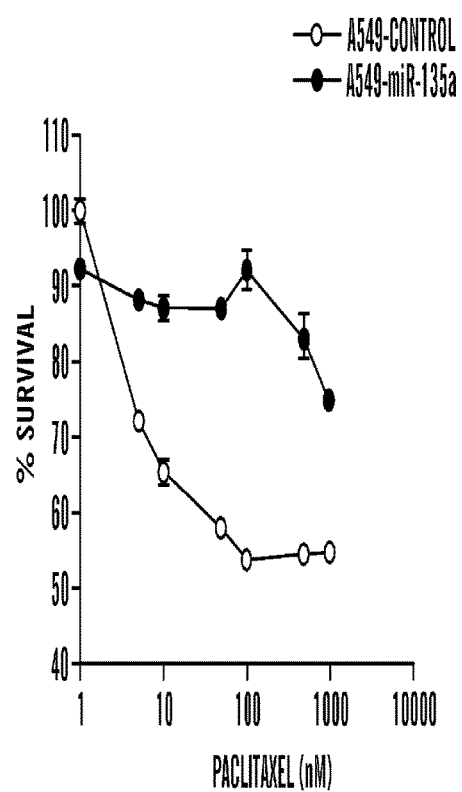
*FIG. 8A*  *FIG. 8B*

DIAGNOSIS AND TREATMENT OF TAXANE-RESISTANT CANCERS

CROSS-REFERENCE TO RELATED APPLICATIONS

This application is a national stage filing under 35 U.S.C. 371 of International Application PCT/US2012/032067, filed Apr. 4, 2012, which claims benefit under 35 U.S.C. §119(e) of the U.S. Provisional Application No. 61/471,565, filed Apr. 4, 2011, the contents of which are incorporated herein by reference in their entirety. International Application PCT/US2012/032067 was published under PCT Article 21(2) in English.

GOVERNMENT SUPPORT

This invention was made with Government support under CA37393 awarded by the National Institutes of Health (NIH). The Government has certain rights in the invention.

FIELD OF THE INVENTION

The methods and assays described herein relate to the diagnosis and treatment of taxane-resistant cancers.

BACKGROUND

Taxanes, such as paclitaxel, docetaxol and cabazitaxel, exert their cytotoxic effects via interaction with tubulin subunits, the building blocks of microtubules. Microtubules, formed by polymerization of heterodimeric α- and β-tubulin subunits, play fundamental roles in a wide range of cellular processes, such as maintenance of cell shape, cell signaling and cell division (Gelfand and Bershadsky, 1991). By stabilizing microtubules and inhibiting disassembly to tubulin monomers, taxanes interfere with proper formation of the mitotic spindle, resulting in activation of the mitotic spindle check point and mitotic arrest (Schiff et al., 1979). Drug-treated cells eventually escape mitotic arrest without assembling a normal mitotic spindle. Depending on the cell type and concentration of taxanes used, these cells will either undergo apoptosis during mitotic arrest or as a result of the abnormal mitosis (Shi et al., 2008). The mechanisms of taxane-induced apoptosis are poorly understood, but involve both phosphorylation of Bcl-2 and activation of caspases-3 and -9 (Haldar et al., 1996; Perkins et al., 1998).

Since the U.S. Food and Drug Administration (FDA) originally approved paclitaxel for clinical use for advanced ovarian cancer in 1992, it has shown significant activity against a broad spectrum of solid malignancies. At present, taxanes, either as single-agents or in combination with multiple other cytotoxic agents, are routinely used in the adjuvant, neoadjuvant and metastatic setting for a wide range of solid malignancies, including those of the breast, prostate, ovary, lung, and head and neck (Chu et al., 2005; Dombernowsky et al., 1996; Mackler and Pienta, 2005; Wakelee et al., 2005). Despite its widespread use, the clinical effectiveness of taxanes is limited by the emergence of taxane-resistant cancer cells, which ultimately leads to relapse and worsens prognosis.

SUMMARY

The methods and assays described herein are based, in part, on the discovery that the expression level of miR-135a is increased in paclitaxel-resistant cells. Thus, provided herein are methods for diagnosing taxane-resistant cancers by determining the level of expression of miR-135a in a biological sample, e.g., a sample obtained from a subject being treated with a taxane. Also provided herein are methods for treating cancer by administering an inhibitor of the miR-135a pathway and a taxane to a subject in need thereof.

In one aspect, the methods provided herein relate to a method for treating taxane-resistant cancer, the method comprising: administering a taxane and an inhibitor of the miR-135a pathway to a subject having taxane-resistant cancer, thereby treating the taxane-resistant cancer.

In one embodiment of this aspect and all other aspects described herein, the inhibitor comprises an antagomir, an oligonucleotide, or a small molecule.

In another embodiment of this aspect and all other aspects described herein, the inhibitor of the miR-135a pathway is an inhibitor of miR-135a. In some embodiments, an inhibitor of the miR-135a pathway is used in combination with an inhibitor of prohibitin.

In another embodiment of this aspect and all other aspects described herein, the taxane is paclitaxel, docetaxel, cabazitaxel, or a derivative or analog thereof.

In another embodiment of this aspect and all other aspects described herein, the taxane-resistant cancer comprises a prostate cancer, a breast cancer, a uterine cancer, an ovarian cancer, a lung cancer, a bladder cancer, a prostate cancer, a melanoma, a head and neck cancer or an esophageal cancer.

In other embodiments of this aspect and all other aspects described herein, the taxane is administered: (i) simultaneously with administration of the inhibitor of the miR-135a pathway; (ii) prior to administration of the inhibitor of the miR-135a pathway; or (iii) following administration of the inhibitor of the miR-135a pathway.

In some embodiments of this aspect and all other aspects described herein, the taxane and the inhibitor of the miR-135a pathway are administered in the same composition or different compositions. In such embodiments, administration the inhibitor of the miR-135a pathway can be separated from the administration of the taxane by at least 1 hour, at least 2 hours, at least 6 hours, at least 12 hours, at least 24 hours, at least 36 hours, at least 72 hours, or at least 1 week.

In some embodiments of this aspect and all other aspects described herein, the subject is human.

Another aspect described herein relates to a method of killing a taxane-resistant cancer cell, the method comprising: contacting the cell with a taxane and an inhibitor of an miR-135a pathway, thereby killing the cell.

In some embodiments of this aspect and all other aspects described herein, the inhibitor comprises an antagomir, an oligonucleotide, or a small molecule. In one such embodiment, the inhibitor of the miR-135a pathway is an inhibitor of miR-135a. In some embodiments, an inhibitor of the miR-135a pathway is used in combination with an inhibitor of prohibitin.

In another embodiment of the methods described herein, the taxane is paclitaxel, docetaxel, cabazitaxel, or a derivative or analog thereof.

In some embodiments of this aspect and all other aspects described herein, the taxane-resistant cancer cell comprises a prostate cancer cell, a breast cancer cell, a uterine cancer cell, an ovarian cancer cell, a lung cancer cell, a bladder cancer cell, a prostate cancer cell, a melanoma cell, a head and neck cancer cell or an esophageal cancer cell.

In some embodiments of this aspect and all other aspects described herein, the taxane is contacted with the taxane-resistant cancer cell: (i) simultaneously with administration of the inhibitor of the miR-135a pathway; (ii) prior to contacting the cell with an the inhibitor of the miR-135a pathway; or (iii) following contacting the cell with the inhibitor of the miR-135a pathway.

In other embodiments of this aspect and all other aspects described herein, the taxane and the inhibitor of the miR-135a pathway are contacted with the cell in the same composition or different compositions.

In another embodiment of this aspect and all other aspects described herein, the step of contacting the cell with the inhibitor of the miR-135a pathway is separated from the step of contacting the cell with the taxane by at least 1 hour, at least 2 hours, at least 6 hours, at least 12 hours, at least 24 hours, at least 36 hours, at least 72 hours, or at least 1 week.

In another embodiment of this aspect and all other aspects described herein, the taxane-resistant cell is human.

Another aspect disclosed herein relates to a method comprising administering an effective therapeutic amount of a taxane and a therapeutically effective amount of an inhibitor of the miR-135a pathway to a subject for treatment of a taxane-resistant cancer, wherein the subject was first determined to have a taxane-resistant cancer.

In some embodiments, an inhibitor of the miR-135a pathway is used in combination with an inhibitor of prohibitin.

In one embodiment of this aspect and all other aspects described herein, the subject is presently receiving treatment with a taxane or was previously treated with a taxane.

In another embodiment of this aspect and all other aspects described herein, the subject was first determined to have a taxane-resistant cancer by comparing the level of miR-135a in a biological sample obtained from the subject to a reference sample, wherein an increase in the level of miR-135a relative to the reference sample indicates that the subject has a taxane-resistant cancer and wherein no change or a decrease in the level of miR-135a relative to the reference sample indicates that the subject has a cancer that is not taxane-resistant.

In another embodiment of this aspect and all other aspects described herein, the reference sample comprises a biological sample obtained from the subject prior to treatment with a taxane.

In another embodiment of this aspect and all other aspects described herein, the reference sample comprises a reference standard obtained from a population of subjects having a taxane-sensitive or taxane-resistant cancer.

In another embodiment of this aspect and all other aspects described herein, the inhibitor comprises an antagomir, an oligonucleotide, or a small molecule.

In another embodiment of this aspect and all other aspects described herein, the taxane is paclitaxel, docetaxol, cabazitaxel, or a derivative or analog thereof.

In another embodiment of this aspect and all other aspects described herein, the taxane-resistant cancer comprises a prostate cancer, a breast cancer, a uterine cancer, an ovarian cancer, a lung cancer, a bladder cancer, a prostate cancer, a melanoma, a head and neck cancer or an esophageal cancer.

In another embodiment of this aspect and all other aspects described herein, the taxane is administered: (i) simultaneously with administration of the inhibitor of the miR-135a pathway; (ii) prior to administration of the inhibitor of the miR-135a pathway; or (iii) following administration of the inhibitor of the miR-135a pathway.

In another embodiment of this aspect and all other aspects described herein, the taxane and the inhibitor of the miR-135a pathway are administered in the same composition or different compositions.

In another embodiment of this aspect and all other aspects described herein, administration the inhibitor of the miR-135a pathway is separated from the administration of the taxane by at least 1 hour, at least 2 hours, at least 6 hours, at least 12 hours, at least 24 hours, at least 36 hours, at least 72 hours, or at least 1 week.

In another embodiment of this aspect and all other aspects described herein, the subject is human.

In another embodiment of this aspect and all other aspects described herein, the inhibitor of the miR-135a pathway is an inhibitor of miR-135a.

Another aspect disclosed herein relates to a method comprising: contacting a nucleic acid sample obtained from a subject being treated with a taxane, with at least one nucleic acid probe to amplify and measure the level of miR-135a in the sample, wherein an increase in the level of miR-135a compared to a reference sample indicates the subject has a taxane-resistant cancer and wherein no change or a decrease in the level of miR-135a compared to the reference sample indicates the subject has a taxane-sensitive cancer.

In another embodiment of this aspect and all other aspects described herein, the subject determined to have a taxane-resistant cancer is treated with a taxane and an inhibitor of the miR-135a pathway. In some embodiments, an inhibitor of the miR-135a pathway is used in combination with an inhibitor of prohibitin.

In another embodiment of this aspect and all other aspects described herein, the reference sample comprises a biological sample obtained from the subject prior to treatment with a taxane.

In another embodiment of this aspect and all other aspects described herein, the reference sample comprises a reference standard obtained from a population of subjects having a taxane-sensitive or taxane-resistant cancer.

In another embodiment of this aspect and all other aspects described herein, the taxane is paclitaxel, cabazitaxel, or docetaxel.

In another embodiment of this aspect and all other aspects described herein, the taxane-resistant cancer comprises a prostate cancer, a breast cancer, a uterine cancer, an ovarian cancer, a lung cancer, a bladder cancer, a prostate cancer, a melanoma, a head and neck cancer or an esophageal cancer.

In another embodiment of this aspect and all other aspects described herein, the subject is human.

Also disclosed herein, in another aspect, is an assay comprising: analyzing a biological sample obtained from a subject being treated with a taxane for the level of miR-135a in the sample, wherein the level of miR-135a is determined by an amplification reaction or binding to a probe, and wherein an increase in the level of miR-135a compared to a reference sample indicates a taxane-resistant cancer and wherein no change or a decrease in the level of miR-135a compared to the reference sample indicates a taxane-sensitive cancer.

In another embodiment of this aspect and all other aspects described herein, the assay further comprises instructions to treat a taxane-resistant cancer with a therapeutically effective amount of a taxane in combination with a therapeutically effective amount of an inhibitor of the miR-135a pathway. In some embodiments, an inhibitor of the miR-135a pathway is administered in combination with an inhibitor of prohibitin.

In another embodiment of this aspect and all other aspects described herein, the amplification reaction comprises a polymerase chain reaction.

In another embodiment of this aspect and all other aspects described herein, the reference sample comprises a biological sample obtained from the subject prior to treatment with a taxane.

In another embodiment of this aspect and all other aspects described herein, the reference sample comprises a reference standard obtained from a population of subjects having a taxane-sensitive or taxane-resistant cancer.

In another embodiment of this aspect and all other aspects described herein, the taxane is paclitaxel, docetaxel, cabazitaxel, or a derivative or analog thereof.

In another embodiment of this aspect and all other aspects described herein, the taxane-resistant cancer comprises a prostate cancer, a breast cancer, a uterine cancer, an ovarian cancer, a lung cancer, a bladder cancer, a prostate cancer, a melanoma, a head and neck cancer or an esophageal cancer.

In another embodiment of this aspect and all other aspects described herein, the subject is human.

Another aspect disclosed herein relates to a method for monitoring efficacy of a taxane, the method comprising: comparing the level of miR-135a in a biological sample obtained from a subject being treated with a taxane with a reference sample, wherein an increase in the level of miR-135a compared to a reference sample indicates a taxane-resistant cancer and wherein no change or a decrease in the level of miR-135a compared to the reference sample indicates a taxane-sensitive cancer.

Also disclosed herein, in another aspect, are kits comprising: (i) primers for amplifying miR-135a or a labeled probe for detecting miR-135a, (ii) a reference sample comprising a known quantity of miR-135a, and (iii) instructions for detecting a taxane-resistant cancer.

Another aspect disclosed herein relates to a computer readable storage medium having computer readable instructions recorded thereon to define software modules for implementing on a computer a method for assessing the expression level of miR-135a in a biological sample, said computer readable storage medium comprising: (a) instructions for storing and accessing data representing the expression level of miR-135a obtained from a subject having cancer; (b) instructions for comparing said expression level of miR-135a to a reference standard stored on said storage device using a comparison module, (c) instructions for displaying retrieved content to a user, wherein the retrieved content comprises an increase, decrease or no change in the level of miR-135a.

In one embodiment of this aspect and all other aspects described herein, the reference standard is obtained from a plurality of subjects having a taxane-resistant or a taxane-sensitive cancer.

In another embodiment of this aspect and all other aspects described herein, an increase in the level of miR-135a compared to the reference standard indicates a taxane-resistant cancer and wherein no change or a decrease in the level of miR-135a compared to the reference standard indicates a taxane-sensitive cancer.

Also disclosed herein, in another aspect, are computer systems for obtaining data from a biological sample obtained from a subject being treated for cancer, the system comprising: (a) a specimen container to hold said sample; (b) a determination module configured to determine read-out information, wherein said read-out information comprises information representing the expression level of miR-135a, (c) a storage device configured to store data output from said determination module, (d) a comparison module adapted to compare the data obtained from said determination module with reference data on said storage device, whereby a change in the expression level of miR-135a is determined; (e) a display module for displaying retrieved content to the user, wherein the retrieved content comprises an increase, decrease or no change in the level of miR-135a.

In another embodiment of this aspect and all other aspects described herein, an increase in the level of miR-135a compared to the reference standard indicates a taxane-resistant cancer and wherein no change or a decrease in the level of miR-135a compared to the reference standard indicates a taxane-sensitive cancer.

BRIEF DESCRIPTION OF THE FIGURES

FIGS. 2A-2D are a series of bar graphs indicating that miR-135a is functionally involved in the paclitaxel response of cancer cell lines. The paclitaxel-resistant cell lines MES-SA$^{DX5}$ and A549$^{TR}$ were transfected with a scrambled non-targeting miRNA (control) and an miR-135a mimic (mimic), respectively. Cells were subsequently treated with 100 nM paclitaxel and cell viability was assessed using the MTT assay (FIGS. 2A, 2B). The percentage of apoptotic cells was assessed by Annexin V-staining and FACS analysis (FIGS. 2C, 2D). Values are presented as percent cell survival in paclitaxel-treated cells relative to untreated cells. *P<0.05, **P<0.001 as determined by Wilcoxon's rank sum test.

FIGS. 3A-3E are a series of bar graphs showing that miR-135a modulates APC expression in paclitaxel-resistant cancer cells. MES-SA (FIG. 3A) or A549 (FIG. 3B) cells were transfected with a luciferase reporter construct fused to APC 3'-UTR or a control luciferase reporter vector with a random 3'-UTR (random UTR). Subsequently, cells were cotransfected with either an miR-135a mimic or a non-targeting miRNA control (control miRNA). Values are shown as the percent of luciferase expression compared with the control. *P<0.01 as determined by Wilcoxon's rank sum test. FIG. 3C: Endogenous APC mRNA expression was quantified by RT-PCR analysis in A549, A549$^{TR}$, MES-SA and MES-SA$^{DX5}$ cells. Bars represent mean and s.e.m. from duplicate experiments. NS: not significant, **P<0.001 as determined by Wilcoxon's rank sum test. In addition, APC protein expression was examined by western blotting (bottom panel). FIG. 3D: A549TR cells were transfected with scrambled non-targeting miRNA (control) or miR-135a inhibitor. At the indicated time points, APC mRNA expression was examined by qRT-PCR. In addition, A549TR cells were mock-transfected, transfected with a scrambled miRNA (control inhibitor) or with a miR-135a inhibitor (FIG. 3E). Cells were fixed with paraformaldehyde, permeabilized and stained with APC-specific polyclonal antibodies, followed by fluorophore conjugated secondary antibodies; nuclei were stained with DAPI (FIG. 3E). In addition, cells were lysed and APC protein levels were examined by western blot (FIG. 3E).

(FIG. 4D) Western blot analysis shows the expression level of APC in both cells. (FIG. 4E) Both A549-shCON and -shAPC cells were treated with paclitaxel and cell viability was measured using the MTT assay. Values are presented as percentage of cell survival in paclitaxel-treated cells relative to untreated cells.

FIGS. 5A-5C show an exemplary protocol for establishing A549 paclitaxel-resistant cells in vivo. (FIG. 5A) A suspension of A549 cells was injected subcutaneously into the flank of a nude mouse. When the average tumor volume was at least 120 mm$^3$, vehicle or paclitaxel (15 mg/kg) was administered intraperitoneally every other day. Treatment was continued until tumors reached approximately four times their initial volume. Paclitaxel-refractory, as well as vehicle-treated tumors, were digested with collagenase and cultured in vitro (adapted from Norman E et al. *Nature Reviews Drug Discovery* 2006; 5: 741-754). (FIG. 5B) Tumor growth was determined as the tumor volume on the day of treatment relative to the tumor volume at the start of treatment and presented as a ratio. Each line represents the growth of an individual tumor (T) in an individual mouse (indicated by a number). Groups of mice are separated into control, paclitaxel-responsive and paclitaxel non-responsive (continuous tumor growth in the presence of paclitaxel) groups. Curves for representative tumors per group are shown. (FIG. 5C) Vehicle-treated tumors (hatched bars) or paclitaxel-refractory tumors (black bars) were harvested from mice and used to generate two cell lines per tumor. The indicated cell lines were cultured in vitro and cell viability was assessed 72 h after paclitaxel addition using the MTT assay. Bars represent average LC50±s.e.m. from triplicate experiments. The most resistant and sensitive cell lines in vitro, indicated with a checkmark, were selected for reinjection.

(FIG. 6A) Tumor cell lines established after an initial round of inoculation and treatment with either vehicle (T28.2) or 15 mg/kg paclitaxel (T20.2) were harvested during log-phase growth and reinjected subcutaneously into the flanks of nude mice. When the average tumor volume was ~120 mm$^3$, vehicle (open circles or squares) or 15 mg/kg paclitaxel (closed circles or squares) was administered intraperitoneally every other day. Treatment was continued until tumors reached approximately four times their initial volume. Each curve represents the average tumor growth±s.e.m. for 10 mice per group. FIG. 6B shows the relative tumor burden at the end of the experiment. Each bar represents the average tumor growth±s.e.m. for 10 mice per group. NS: not significant, *P<0.05 as determined by Wilcoxon's rank sum test. (FIG. 6C) Tumors were harvested, cultured in vitro and cell viability was assessed using the MTT assay. Values are presented as percentage of cell survival in paclitaxel-treated cells relative to untreated cells. White bars represent LC50s from tumor cell lines established from T28.2 tumors treated with vehicle. Black bars represent LC50s from cell lines established from T20.2 tumors treated with paclitaxel. Shown are the mean±s.e.m. of two independent experiments, each performed in triplicate. *P<0.05 as determined by Wilcoxon's rank sum test.

FIGS. 7A-7E are a series of graphs indicating that miR-135a has a role in in vivo paclitaxel resistance. (FIG. 7A). The parental A549 cells, a cell line that became refractory during in vivo treatment with paclitaxel (T20.2 round 1) and the same cell line established after yet another round of in vivo paclitaxel treatment (T20.2 reinjection) were treated with paclitaxel and cell viability was assessed using the MTT assay. Represented are average LC50±s.e.m. determined by MTT assay for parental A549 cells (white boxes), **P<0.001, *P<0.05 as determined by Wilcoxon's rank sum test for T20.2 round 1 cells (hatched boxes) and for T20.2 re-injection cells (filled boxes). (FIG. 7B) The expression of miR-135a was examined in these cells by qRT-PCR. *P<0.05 as determined by Wilcoxon's rank sum test. (FIG. 7C) The expression of miR-135a was examined in the cell lines established in vivo. The correlation between paclitaxel response and miR-135a expression was calculated using the Spearman's rank test. (FIGS. 7D, 7E) The paclitaxel-resistant cell line T800.1 (FIG. 7D) or the paclitaxel-sensitive T824.1 cell line (FIG. 7E) established after two rounds of treatment with vehicle were transfected with a scrambled non-targeting miRNA (control), a miR-135a inhibitor (inhibitor) in the resistant cells or a miR-135a mimic (mimic) in the sensitive cells. Subsequently, cells were treated with the indicated concentrations of paclitaxel and cell viability was assessed using the MTT assay. Values are presented as percentage of cell survival in paclitaxel-treated cells relative to untreated cells. Shown are the mean and s.e.m. of two independent experiments, each performed in triplicate.

FIGS. 8A-8D shows that overexpression of miR-135a confers paclitaxel resistance in A549 cells in vivo. A549 cells stably expressing either non-targeting premiR (A549-control) or premiR-135a (A549-miR-135a) were generated. (FIG. 8A) miR-135a expression level in A549-control and -miR-135a was determined and compared with A549 and A549TR cells using qRT-PCR analysis. *P<0.01. (FIG. 8B) Paclitaxel response of A549-control and A549-premiR-135a cells was determined using the MTT assay. (FIG. 8C) APC protein expression was examined using western blot analysis in A549-control and -premiR-135a cells. (FIG. 8D) A549-control and -premiR-135a cells were inoculated subcutaneously into the flanks of nude mice. Paclitaxel treatment was given three times a week for 3 weeks. The tumor size in each group was measured during the course of treatment and was calculated, relative to the size before treatment initiation. Each curve represents the average tumor growth±s.e.m. for 10 mice per group. **P<0.001 as determined by Wilcoxon's rank sum test.

DETAILED DESCRIPTION

Figure 1:
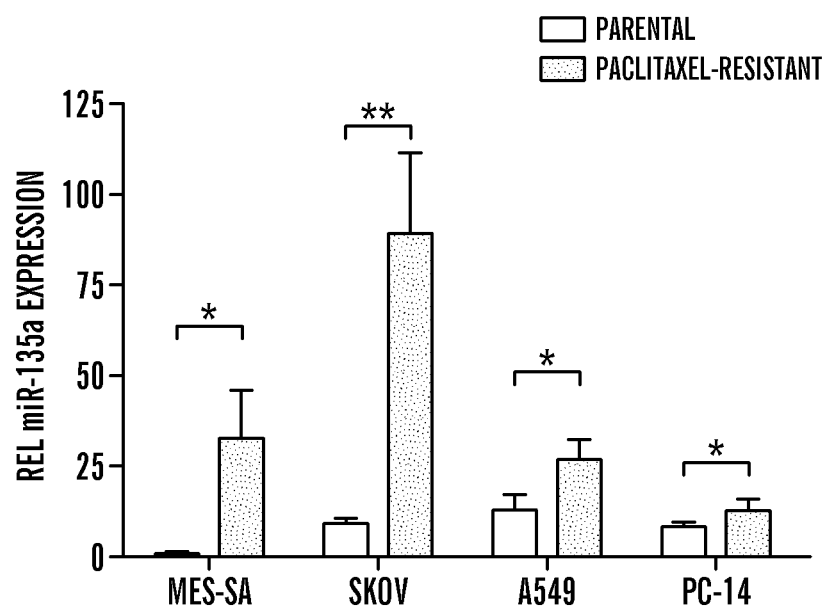
FIG. 1 is a bar graph depicting upregulation of miR-135a in a panel of paclitaxel-resistant cancer cell lines. RT-PCR analysis of miR-135a expression in parental MES-SA, SKOV, A549, and PC-14 cells (gray bars) compared with the expression of their paclitaxel-resistant subclones (black bars). Bars represent mean and % s.e.m. from triplicate experiments. *P<0.05, **P<0.001 as determined by Wilcoxon's rank sum test.

Provided herein are methods and assays relating to the diagnosis and treatment of taxane-resistant cancers. Such methods and assays comprise determining the level of expression of miR-135a in a biological sample from a subject suspected of having a taxane-resistant cancer, or previously or currently being treated with a taxane anti-cancer agent. Also provided herein are methods for treating cancer by administering an inhibitor of the miR-135a pathway and a taxane to a subject in need thereof.

Definitions

The terms "microRNA" or "miRNA" are used interchangeably herein refer to endogenous RNAs, some of which are known to regulate the expression of protein-coding genes at the posttranscriptional level.

As used herein, the term "a taxoid family member" or "taxoid compound" or "taxane" refers to a class of chemotherapeutic compounds belonging to the taxane family. Specific members of the taxane family include, but are not limited, to paclitaxel (Taxol™), docetaxel (Taxotere™), cabazitaxel (Jevtana™; XRP-6258), and analogs thereof (i.e., XRP9881; see Ojima and Geney, *Curr Opin Investig Drugs* 4:73 7, 2004). Members of this class of molecules are β-tubulin binders and stabilize microtubules in a polymerized form.

As used herein, the term "taxane-resistant cancer" refers to a tumor or cancer that does not respond or is no longer responsive to treatment with a taxane anti-cancer therapy. A cancer or tumor can be determined to be non-responsive to treatment with a taxane by e.g., assessing standard clinical indicators including but not limited to, little to no decrease (or an increase) in tumor size, presence or emergence of metastases, no decrease (or an increase) in tumor growth rate, or as described herein in the Examples section by determining the expression level of miR-135a in a biological sample.

As used herein, the term "inhibitor of the miR-135a pathway" refers to an inhibitor of miR-135a or a member of a downstream signaling pathway of miR-135a (e.g., APC). An inhibitor can be e.g., an antagomir, an oligonucleotide, an antibody, an RNA interference molecule (e.g., siRNA, shRNA etc.) or a small molecule, among others.

As used herein, the terms "biological sample" refers to a fluid sample, a cell sample, a tissue sample or an organ sample obtained from a subject or patient. In some embodiments, a cell or population of cells, an exosome, or a quantity of tissue or fluid are obtained from a subject. Biological samples include, but are not limited to, tissue biopsies, tumor biopsies, scrapes (e.g. buccal scrapes), whole blood, plasma, serum, urine, saliva, cell culture, intestinal lavage, cerebrospinal fluid, circulating tumor cells, and the like. For the purpose of the present disclosure, a biological sample comprises at least one cancer cell. Samples can include frozen or paraffin-embedded tissue. The term "sample" includes any material derived by processing such a sample. Derived samples may, for example, include nucleic acids or proteins extracted from the sample or obtained by subjecting the sample to techniques such as amplification or reverse transcription of mRNA, isolation and/or purification of certain components, etc.

As used herein, the term "reference" refers to a reference value, or range of values, obtained for miR-135a from e.g., at least one subject determined to lack a taxane-resistant cancer. The reference value or range of values can be obtained from a plurality of subjects in a population substantially free of taxane-resistant cancer (i.e., cancer is not detectable by typical clinical means) or alternatively from a plurality of subjects in a population having a taxane-resistant cancer. The reference sample can be stored as a value(s) on a computer or PDA device to permit comparison with a value obtained from a subject using the methods described herein. The reference sample can also be obtained from the same subject e.g., at an earlier time point prior to onset of taxane resistance or prior to initiation of treatment with a taxane using clinical tests known to those of skill in the art. One of skill in the art can determine an appropriate reference sample for use with the methods described herein. In one embodiment, the reference is obtained from a subject or plurality of subjects having, or diagnosed with having, a taxane-resistant cancer or a taxane-sensitive cancer.

As used herein, the terms "chemotherapy" or "chemotherapeutic agent" refer to any chemical agent with therapeutic usefulness in the treatment of diseases characterized by abnormal cell growth. Such diseases include tumors, neoplasms and cancer as well as diseases characterized by hyperplastic growth. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed., ©2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993).

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a malignant condition or cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but can also include a cessation or at least slowing of progress or worsening of symptoms that would be expected in absence of treatment. Beneficial or desired clinical results include, but are not limited to, alleviation of one or more symptom(s) of a malignant disease, diminishment of extent of a malignant disease, stabilized (i.e., not worsening) state of a malignant disease, delay or slowing of progression of a malignant disease, amelioration or palliation of the malignant disease state, and remission (whether partial or total), whether detectable or undetectable. The term "treatment" of a disease also includes providing relief from the symptoms or side-effects of the disease (including palliative treatment).

As used herein, the term "therapeutically effective amount" means that amount necessary, at least partly, to attain the desired effect, or to delay the onset of, inhibit the progression of, or halt altogether, the onset or progression of the particular disease or disorder being treated (e.g., taxane-resistant cancer). Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. In some embodiments, a maximum dose of the anti-cancer agent is used, that is, the highest safe dose according to sound medical judgment. It will be understood by those of ordinary skill in the art, however, that a lower dose or tolerable dose can be administered for medical reasons, psychological reasons or for virtually any other reason.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level or non-detectable level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

The term "statistically significant" or "significantly" refers to statistical significance and generally means a two standard deviation (2SD) below normal, or lower, e.g., level of miR-135a expression. The term refers to statistical evidence that there is a difference. It is defined as the probability of making a decision to reject the null hypothesis when the null hypothesis is actually true. The decision is often made using the p-value.

As used herein, the term "serially monitoring" when referring to a level of miR-135a in a sample, refers to measuring a level of miR-135a in a sample obtained from a subject on two or more occasions (e.g., doctor's visits). Serial monitoring can be performed on samples obtained from subjects on a quarterly, bimonthly, monthly, biweekly, weekly, every 3 days or on a daily basis. Serial monitoring of a level of miR-135a includes periodically measuring a level of miR-135a at regular intervals as deemed necessary by the skilled artisan.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Taxanes and Taxane Resistance

Taxanes, such as paclitaxel, cabazitaxel, and docetaxel, exert their cytotoxic effects via interaction with tubulin subunits, the building blocks of microtubules. Microtubules, formed by polymerization of heterodimeric α- and β-tubulin subunits, play fundamental roles in a wide range of cellular processes, such as maintenance of cell shape, cell signaling and cell division (Gelfand and Bershadsky, 1991). By stabilizing microtubules and inhibiting disassembly to tubulin monomers, taxanes interfere with proper formation of the mitotic spindle, resulting in activation of the mitotic spindle check point and mitotic arrest (Schiff et al., 1979). Drug-treated cells eventually escape mitotic arrest without assembling a normal mitotic spindle. Depending on the cell type and concentration of taxanes used, these cells will either undergo apoptosis during mitotic arrest or as a result of the abnormal mitosis (Shi et al., 2008). The mechanisms of taxane-induced apoptosis are poorly understood, but involve both phosphorylation of Bcl-2 and activation of caspases-3 and -9 (Haldar et al., 1996; Perkins et al., 1998). Taxane compounds include, but are not limited to, paclitaxel (Taxol™), docetaxol (Taxotere™), cabazitaxel (Jevtana™), and analogs thereof.

Docetaxel inhibits microtubule dynamics by binding to beta-tubulin and blocking disassembly of alpha- and beta-tubulin heterodimers thus abrogating tumor growth. Docetaxel has been approved for the treatment of breast cancer, non-small cell lung cancer, advanced stomach cancer, head and neck cancer and metastatic prostate cancer. Docetaxel is also being investigated to treat small cell lung, ovarian, bladder, and pancreatic cancers, soft tissue sarcoma and melanoma.

Paclitaxel (Taxol™) is a complex diterepene derived from the Pacific yew tree *Taxus brevifolia* that also has significant anti-tumor activity. Paclitaxel primarily suppresses microtubule dynamics and interferes with spindle formation arresting cell cycle at mitosis leading to apoptosis. Paclitaxel is typically used for the treatment of breast, ovarian, lung, bladder, prostate, melanoma, esophageal, as well as other types of solid tumor cancers. It has also been used in Kaposi's sarcoma.

Cabazitaxel is a semi-synthetic taxane that has been approved for use in the treatment of hormone refractory prostate cancer or castrate-resistant prostate cancer.

As with many cancer therapeutic agents, resistance to taxane family members remains a significant hindrance in their application as successful chemotherapeutic drugs. Resistance to the taxane compounds can be either inherent or acquired subsequent to treatment most likely due to emergence of a minority population. For example, paclitaxel resistance is believed to be a multifactorial phenomenon. The principle mechanisms underlying resistance include the overexpression of transporter protein P-glycoprotein, altered binding of paclitaxel to its cellular target, β-tubulin, mutations in the β-tubulin gene, overexpression of β-tubulin isotypes, and decreased sensitivity to apoptotic stimuli. The role of P-glycoprotein as a potential mediator of resistance has been abundantly studied. Several P-glycoprotein inhibitors have been characterized although relatively few of these, such as verapamil and cyclosporine, have shown any clinical efficacy and are frequently accompanied by dose-limiting side effects. Recently, there has been renewed effort to find novel effectors of drug resistance which could provide alternative strategies for resistance reversal.

Taxane-Resistant Cancer

Essentially any type of cancer treatable with a taxane compound is at risk for and can acquire taxane-resistance. Thus, the methods and assays described herein can be used to monitor the efficacy of a taxane anti-cancer agent in a subject being treated with the taxane agent. In addition, the methods and assays described herein can also be used to diagnose a taxane-resistant cancer in a subject who is undergoing or who has undergone cancer therapy with a taxane. Further, the methods and assays provided herein also permit treatment of a cancer determined to be taxane-resistant by using an inhibitor of the miR-135a pathway e.g., as an adjunct to taxane therapy.

One of skill in the art will recognize that a variety of subjects can be tested for taxane-resistant cancer. For example, the methods and assays described herein are useful for determining the presence of a taxane-resistant cancer in a subject who has not been treated with a taxane; that is, the subject has a congenital or pre-existing form of taxane-resistance that is not brought on by extended treatment with a taxane compound. In addition, the methods and assays described herein are useful for detecting and/or treating a taxane-resistant cancer in a subject who is undergoing or has undergone treatment with a taxane. The subject's taxane therapy may have been discontinued for hours, days, weeks, months or even years prior to detection of a taxane-resistant cancer and/or initiation of a treatment for taxane-resistance cancer as described herein. Such treatments for taxane-resistant cancer comprise, in part, administration of an inhibitor of the miR-135a pathway and a taxane. Alternatively, treatment with an miR-135a pathway inhibitor can be initiated prior to treatment with a taxane to prevent the development of taxane-resistance cancer cells.

In instances of concurrent administration, the miR-135a pathway inhibitor can continue to be administered after the cancer therapy has ceased. In other embodiments, the miR-135a pathway inhibitor is administered after cancer therapy has ceased (i.e., with no period of overlap with the cancer treatment). The miR-135a pathway inhibitor can be administered immediately after cancer therapy has ceased, or there can be a gap in time (e.g., up to about a day, a week, a month, six months, or a year) between the end of cancer therapy and the administration of the treatment comprising a miR-135a pathway inhibitor. Treatment with the miR-135a pathway inhibitor can continue for as long as necessary to prevent recurrence of and/or treat a taxane-resistant cancer and can be maintained (e.g., up to about a day, a week, a month, six months, a year, two years, three years, four years, five years, or longer).

In one aspect, the methods and assays described herein are useful for diagnosis or treatment of taxane-resistant cancer in a cancer patient who had previously undergone cancer therapy (for example, treatment with a chemotherapeutic (including small molecules and biotherapeutics, e.g., antibodies), radiation therapy, surgery, RNAi therapy and/or antisense therapy) by administering a therapeutically effective amount of a miR-135a pathway inhibitor to the patient after the cancer therapy has ceased. The miR-135a pathway inhibitor can be administered immediately after cancer therapy has ceased, or there can be a gap in time (e.g., up to about a day, a week, a month, six months, or a year) between the end of cancer therapy and the administration of the miR-135a pathway inhibitor.

The methods and assays are useful in preventing, treating, or monitoring a taxane-resistant cancer, particularly the cancers that are commonly treated clinically with taxane compounds. Examples of such cancers include lung cancer (e.g., small cell lung cancer or non-small cell lung cancer), pancreatic cancer, bladder cancer, ovarian cancer, breast cancer, colon cancer, stomach cancer, head and neck cancer, prostate cancer (e.g., castrate-resistant prostate cancer, or hormone refractory prostate cancer), urinary tract cancer, melanoma, esophageal cancer, solid tumor cancer, Kaposi's sarcoma, neuroendocrine cancer, among others.

In some embodiments, the level of miR-135a and the level of prohibitin are determined in the same biological sample or in different biological samples obtained from the same subject on the same occasion (e.g., doctor's visit). Taxane-resistance can be determined by combining the predictive power of an increase in miR-135a expression with that of an increase in prohibitin expression. That is, miR-135a and prohibitin can be used as a panel to diagnose or predict the development of a taxane-resistant cancer.

Obtaining a Biological Sample

A biological sample can be obtained from essentially any tissue comprising or suspected of comprising cancerous cells. Some non-limiting examples of tissues include e.g., brain, liver, lung, gut, stomach, fat, muscle, spleen, testes, uterus, urinary tract, bladder, prostate, esophagus, ovary, skin, endocrine organ and bone, etc. In one embodiment, a biological sample comprises cells including, but not limited to, epithelial, endothelial, neuronal, adipose, cardiac, skeletal muscle, fibroblast, immune cells, hepatic, splenic, lung, circulating blood cells, reproductive cells, gastrointestinal, renal, bone marrow, and pancreatic cells. In one embodiment, the biological sample is a biopsy from a growth or tumor. In another embodiment, the biological sample comprises circulating tumor cells. In another embodiment, the biological sample comprises exosomes.

In one embodiment, the biological sample comprises a tissue biopsy, such as, an aspiration biopsy, a brush biopsy, a surface biopsy, a needle biopsy, a punch biopsy, an excision biopsy, an open biopsy, an incision biopsy or an endoscopic biopsy, or a tumor sample. Biological samples can also be biological fluid samples, including but not limited to, urine, blood, serum, platelets, saliva, cerebrospinal fluid, nipple aspirates, circulating tumor cells, and cell lysate (e.g. supernatant of whole cell lysate, microsomal fraction, membrane fraction, exosomes, or cytoplasmic fraction). Samples can be obtained by any method known to one of skill in the art including e.g., needle biopsy, fine needle aspiration, core needle biopsy, vacuum assisted biopsy, open surgical biopsy, among others.

One of skill in the art will recognize that separate biological samples can be obtained for monitoring levels of an additional biomarker (e.g., prohibitin) alongside the level of miR-135a, for example, if the additional biomarker is monitored at the protein level while miR-135a is monitored at the RNA level. Alternatively, the levels of miR-135a can be measured in the same biological sample as that used to measure the level of the additional biomarker. If separate biological samples are used, they can be obtained at the same time, or at different intervals.

Detection of miR-135a

MicroRNAs (miRNAs) are a growing class of small non-protein coding RNAs that negatively modulate expression of cognate mRNAs (Erson and Petty, 2009). They act by targeting the RNA-induced silencing complex (RISC) to complementary sites within the 3' untranslated region (UTR) of their target mRNAs. Depending on the degree of base pairing between the miRNA and the 3' UTR, either degradation or translational repression of the targeted mRNA will occur. Although they account for less than 1% of all human genes, miRNAs have been estimated to regulate up to 30% of all protein-encoding genes (Xie et al., 2005). Altered miRNA expression has been observed in various human malignancies (Esquela-Kerscher and Slack, 2006; Iorio et al., 2005). Surprisingly, miRNA expression profiles predict tumor type and stage in human cancers more accurately than classical mRNA expression profiles (Lu et al., 2005). The significant correlation between microRNA expression patterns and compound potency in the NCI-60 panel of cell lines suggested that microRNAs may have a role in chemoresistance (Blower et al., 2007). Indeed, various miRNAs were shown to be involved in tumor response to chemotherapy, including paclitaxel (Cochrane et al., 2009; Fujita et al., 2010; Kovalchuk et al., 2008; Sorrentino et al., 2008; Xia et al., 2008; Zhou et al., 2010). All studies to date have been performed using in vitro established paclitaxel-resistant cell lines.

Several nucleic acid assay technologies are useful for identifying and characterizing miRNAs including, but not limited to, microarray and quantitative real-time reverse transcriptase polymerase chain reaction (qRT-PCR) assays. Such methods are useful to identify changes in expression or compare expression profiles obtained from a biological sample e.g., a tumor sample) to a reference (Szafranzka et al., Oncogene 26:4442-4452 (2007); Mattie et al., Molecular Cancer 5:24 (2006); Bandres et al., Molecular Cancer 5:29 (2006); Cummins et al., Proc. Natl. Acad. Sci. 103:3687-3692 (2006); Zhang et al., Proc. Natl. Acad. Sci. 103:9136-9141 (2006); U.S. Pat. No. 7,998,677; US2006/099619; and US2009/0075258). q-PCR is very sensitive, and also has the advantage of high specificity for the detection of an miRNA.

In some embodiments of the methods and assays described herein, detection of the miRNA nucleic acid sequences (e.g., mature miRNAs, precursor miRNAs, and primary miRNAs) comprises amplification. Suitable nucleic acid polymerization and amplification techniques include reverse transcription (RT), polymerase chain reaction (PCR), real-time PCR (quantitative PCR (q-PCR)), nucleic acid sequence-base amplification (NASBA), ligase chain reaction, multiplex ligatable probe amplification, invader technology (Third Wave), rolling circle amplification, in vitro transcription (IVT), strand displacement amplification, transcription-mediated amplification (TMA), RNA (Eberwine) amplification, and other methods that are known to persons skilled in the art. In certain embodiments, more than one amplification method is used, such as reverse transcription followed by real time PCR (Chen et al., Nucleic Acids Research, 33(20):e179 (2005)). Since mature miRNAs are single-stranded, a reverse transcription reaction (which produces a complementary cDNA sequence) is generally performed prior to PCR reactions. Reverse transcription reactions include the use of, e.g., a RNA-based DNA polymerase (reverse transcriptase) and a primer. Standard methods for PCR and other amplification reactions are known to those of skill in the art and thus are not described in detail herein.

In some embodiments, two or more miRNAs are amplified in a single reaction volume (e.g., using a multiplex amplification reaction). For example, multiplex qRT-PCR has research and diagnostic uses, including, but not limited to, detection of miRNAs for diagnostic, prognostic, and therapeutic applications. In one embodiment, the expression level of a target miRNA (e.g., miR-135a) is normalized to e.g., an oncomir, or a reference sample (see e.g., US2009/0075258). In some embodiments, the level of expression of prohibitin is measured and/or monitored in the same biological sample obtained from the subject (e.g., serum). Methods for measuring prohibitin in biological samples are known in the art (see e.g., US2009/0312405, herein incorporated by reference in its entirety).

In certain embodiments, labels, dyes, or labeled probes and/or primers are used to detect amplified or unamplified miRNAs. In some embodiments, such methods can be combined with the amplification methods described herein, particularly if the sensitivity of the detection method or the abundance of the target miRNA are low. One skilled in the art will recognize the detection methods where miRNA amplification is preferred.

In some embodiments, oligonucleotide probes or primers present in a multiplex amplification are suitable for monitoring the amount of amplification product produced as a function of time. In certain aspects, probes having different single stranded versus double stranded character are used to detect the nucleic acid. Probes include, but are not limited to, the 5'-exonuclease assay (e.g., TaqMan™) probes (see U.S. Pat. No. 5,538,848), stem-loop molecular beacons (see, e.g., U.S. Pat. Nos. 6,103,476 and 5,925,517), stemless or linear beacons (see, e.g., WO 9921881, U.S. Pat. Nos. 6,485,901 and 6,649,349), peptide nucleic acid (PNA) Molecular Beacons (see, e.g., U.S. Pat. Nos. 6,355,421 and 6,593,091), linear PNA beacons (see, e.g. U.S. Pat. No. 6,329,144), non-FRET probes (see, e.g., U.S. Pat. No. 6,150,097), Sunrise™/AmplifluorB™probes (see, e.g., U.S. Pat. No. 6,548,250), stem-loop and duplex Scorpion™ probes (see, e.g., U.S. Pat. No. 6,589,743), bulge loop probes (see, e.g., U.S. Pat. No. 6,590,091), pseudo knot probes (see, e.g., U.S. Pat. No. 6,548,250), cyclicons (see, e.g., U.S. Pat. No. 6,383,752), MGB Eclipse™ probe (Epoch Biosciences), hairpin probes (see, e.g., U.S. Pat. No. 6,596,490), PNA light-up probes, antiprimer quench probes (Li et al., Clin. Chem. 53:624-633 (2006)), self-assembled nanoparticle probes, and ferrocene-modified probes described, for example, in U.S. Pat. No. 6,485,901.

In certain embodiments, one or more of the primers in an amplification reaction can include a label. In yet further embodiments, different probes or primers comprise detectable labels that are distinguishable from one another. In some embodiments a nucleic acid, such as the probe or primer, may be labeled with two or more distinguishable labels.

In certain embodiments, the miR-135a nucleic acid sequence is detected by binding with a labeled probe, and the probe is subsequently detected. In another embodiment, a biotinylated probe is combined with a stretavidin-conjugated dye to detect the bound nucleic acid. The streptavidin molecule binds a biotin label on amplified miRNA, and the bound miRNA is detected by detecting the dye molecule attached to the streptavidin molecule.

In some embodiments, miR-135a is detected using a label, such as a light-emitting, a light-scattering, or a light-absorbing compound, which generates or quenches a detectable fluorescent, chemiluminescent, or bioluminescent signal (see, e.g., Kricka, L., Nonisotopic DNA Probe Techniques, Academic Press, San Diego (1992) and Garman A., Non-Radioactive Labeling, Academic Press (1997).). Fluorescent reporter dyes useful as labels include, but are not limited to, fluoresceins (see, e.g., U.S. Pat. Nos. 5,188,934, 6,008,379, and 6,020,481), rhodamines (see, e.g., U.S. Pat. Nos. 5,366,860, 5,847,162, 5,936,087, 6,051,719, and 6,191,278), benzophenoxazines (see, e.g., U.S. Pat. No. 6,140,500), energy-transfer fluorescent dyes, comprising pairs of donors and acceptors (see, e.g., U.S. Pat. Nos. 5,863,727; 5,800,996; and 5,945,526), and cyanines (see, e.g., WO 9745539), lissamine, phycoerythrin, Cy2, Cy3, Cy3.5, Cy5, Cy5.5, Cy7, FluorX (Amersham), Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, Tetramethylrhodamine, and/or Texas Red, as well as any other fluorescent moiety capable of generating a detectable signal. Examples of fluorescein dyes include, but are not limited to, 6-carboxyfluorescein; 2',4',1,4,-tetrachlorofluorescein; and 2',4',5',7',1,4-hexachlorofluorescein. In certain aspects, the fluorescent label is selected from SYBR-Green, 6-carboxyfluorescein ("FAM"), TET, ROX, VIC™, and JOE. For example, in certain embodiments, labels are different fluorophores capable of emitting light at different, spectrally-resolvable wavelengths (e.g., 4-differently colored fluorophores); certain such labeled probes are known in the art and described above, and in U.S. Pat. No. 6,140,054. A dual labeled fluorescent probe that includes a reporter fluorophore and a quencher fluorophore is used in some embodiments. It will be appreciated that pairs of fluorophores are chosen that have distinct emission spectra so that they can be easily distinguished.

In one embodiment, HARP-like probes, as disclosed in U.S. Publication No. 2006/0078894, can be used to measure the quantity of miRNAs. In another embodiment probe ligation reaction may be used to quantify miRNAs (see e.g., Schouten et al., *Nucleic Acids Research* 30:e57 (2002)).

References or Reference Samples

The terms "reference level," "reference sample," and "reference" are used interchangeably herein and refer to the level of miR-135a expression in a known sample against which another sample is compared (i.e., obtained from a subject having a cancer suspected to be taxane-resistant). A standard is useful for determining the amount of miR-135a or the relative increase/decrease of miR-135a in a biological sample. A standard serves as a reference level for comparison, such that samples can be normalized to an appropriate standard in order to infer the presence, absence or extent of a taxane-resistant cancer in a subject.

In one embodiment, a biological standard is obtained at an earlier time point (presumably prior to the onset of taxane resistance) from the same individual that is to be tested or treated as described herein. Alternatively, a standard can be from the same individual having been taken at a time after the onset or diagnosis of a taxane-resistant cancer. In such instances, the standard can provide a measure of the efficacy of treatment.

A standard level can be obtained, for example, from a known biological sample from a different individual (e.g., not the individual being tested) that is substantially free of a taxane-resistant cancer. A known sample can also be obtained by pooling samples from a plurality of individuals to produce a standard over an averaged population, wherein a standard represents an average level of miR-135a among a population of individuals (e.g., a population of individuals having a taxane-resistant cancer or a population of individuals having a taxane-sensitive cancer). Thus, the level of miR-135a in a standard obtained in this manner is representative of an average level of this marker in a general population of individuals having cancer, or a population of individuals having a taxane-resistant cancer. An individual sample is compared to this population standard by comparing expression of miR-135a from a sample relative to the population standard. Generally, an increase in the amount of miR-135a over the standard (e.g., a reference obtained from subjects having a taxane-sensitive cancer) will indicate the presence of a taxane-resistant cancer, while a decrease in the amount of miR-135a will indicate that the cancer is or remains taxane-sensitive. The converse is contemplated in cases where a standard is obtained from a population of subjects having taxane-resistant cancer. It should be noted that there is often variability among individuals in a population, such that some individuals will have higher levels of miR-135a expression, while other individuals have lower levels of expression. However, one skilled in the art can make logical inferences on an individual basis regarding the detection and treatment of cancer as described herein.

A standard or series of standards can also be synthesized. A known amount of miR-135a (or a series of known amounts) can be prepared within the typical expression range for miR-135a that is observed in a general cancer population. This method has an advantage of being able to compare the extent of disease in one or more individuals in a mixed population. This method can also be useful for subjects who lack a prior sample to act as a standard or for routine follow-up post-diagnosis. This type of method can also allow standardized tests to be performed among several clinics, institutions, or countries etc.

miR-135a Pathway Inhibitors miR-135a inhibitors: By "miR-135a inhibitor" is meant an agent that inhibits the activity of miR-135a. The inhibitory agent can inhibit the activity of the target miRNA by a variety of different mechanisms. In certain embodiments, the inhibitory agent is one that binds to the target miRNA (e.g., miR-135a) and, in doing so, inhibits its activity. Representative miRNA inhibitory agents include, but are not limited to: antisense oligonucleotides, small molecules, and the like.

In one embodiment, the miR-135a inhibitor comprises an inhibitory nucleic acid sequence. miRNA antagonists can be designed such that the antagonist is sufficiently complementary to a portion of the miRNA or a pre-miRNA to be inhibited (e.g., miR-135a). As used herein, the term "sufficiently complementary" means that two sequences can form a duplex through Watson-Crick base pairing under physiologic conditions. An miRNA antagonist sequence that is sufficiently complementary to an miRNA or pre-miRNA target sequence can be 70%, 80%, 90%, or more identical to the miRNA or pre-miRNA sequence. In one embodiment, the miRNA antagonist contains no more than 1, 2 or 3 nucleotides that are not complementary to the miRNA or pre-miRNA target sequence. In another embodiment, the miRNA antagonist is 100% complementary to an miRNA or pre-miRNA target sequence.

In some embodiments, the miRNA antagonists include oligonucleotides comprising at least 6, at least 7, at least 8, at least 9, at least 10, at least 11, at least 12, at least 13, at least 14, at least 15, at least 16, at least 17, at least 18, at least 19, at least 20 or more contiguous nucleotides substantially complementary to an endogenous miRNA or pre-miRNA e.g., miR-135a in a biological sample from a subject suspected of having a taxane-resistant cancer. In some embodiments, the miR-135a inhibitor comprises a nucleotide sequence sufficiently complementary to hybridize to about 12 to 25 nucleotides, preferably about 15 to 23 nucleotides of miR-135a. In some embodiments, nucleotide mismatches can be incorporated into the region of complementarity. In such embodiments, the region of complementarily will have no more than 1, 2, 3, 4, or 5 mismatches.

In one embodiment, the miRNA inhibitor is an oligomer or a polymer of ribonucleic acid (RNA) or deoxyribonucleic acid (DNA), or modifications thereof. Such miRNA inhibitors can include oligonucleotides that contain naturally-occurring nucleobases, sugars and covalent internucleoside (backbone) linkages.

In one embodiment of the methods and assays described herein, an inhibitor of miR-135a is an antagomir. Antagomirs are described, for example, in US2007/0213292. Antagomirs are RNA-like oligonucleotides that contain various modifications for RNase protection and pharmacologic properties that permit enhanced tissue and cellular uptake. Antagomirs differ from normal RNA by having complete 2'-O-methylation of sugar, phosphorothioate backbone and a cholesterol-moiety at 3'-end.

The terms "antimir," "antagomir," "microRNA inhibitor," or "miR inhibitor" are synonymous and refer to oligonucleotides that interfere with the activity of a specific miRNA (e.g., miR-135a) Inhibitors can adopt a variety of configurations including single stranded, double stranded (RNA/RNA or RNA/DNA duplexes), and hairpin designs. In general, microRNA inhibitors comprise one or more sequences or portions of sequences that are complementary, or partially complementary, with the mature strand (or strands) of the miRNA to be targeted. In addition, a miRNA inhibitor can also comprise additional sequences located 5' and 3' to the sequence that is the reverse complement of the mature miRNA. The additional sequences can be the reverse complements of the sequences that are adjacent to the mature miRNA in the pri-miRNA, from which the mature miRNA is derived, or the additional sequences can be arbitrary sequences (having a mixture of A, G, C, U, or dT). In some embodiments, one or both of the additional sequences are arbitrary sequences capable of forming hairpins. Thus, in some embodiments, the sequence that is the reverse complement of the miRNA is flanked on the 5' side and on the 3' side by hairpin structures. MicroRNA inhibitors, when double stranded, can include mismatches between nucleotides on opposite strands.

MicroRNA inhibitors, including hairpin miRNA inhibitors, are known in the art. See Vermeulen et al., 13 RNA 723-30 (2007); WO2007/095387; WO 2008/036825. A person of ordinary skill in the art can design an inhibitor directed to miR-135a that is useful for the methods disclosed herein.

Antagomirs can include a phosphorothioate at least the first, second, or third internucleotide linkage at the 5' or 3' end of the nucleotide sequence. In one embodiment, antagomirs contain six phosphorothioate backbone modifications; two phosphorothioates are located at the 5'-end and four at the 3'-end. Phosphorothioate modifications provide protection against RNase activity and their lipophilicity contributes to enhanced tissue uptake.

Examples of antagomirs and other miRNA inhibitors are described in WO2009/020771, WO2008/091703, WO2008/046911, WO2008/074328, WO2007/090073, WO2007/027775, WO2007/027894, WO2007/021896, WO2006/093526, WO2006/112872, WO2007/112753, WO2007/112754, WO2005/023986, or WO2005/013901.

Custom designed Anti-miR® molecules are commercially available from Applied Biosystems. Thus, in some embodiments, the antagomir is an Ambion® Anti-miR® inhibitor, such as anti-miR-135a. Anti-miR molecules can be chemically modified and optimized to specifically inhibit naturally occurring mature miRNA molecules in cells.

Custom designed Dharmacon Meridian® microRNA Hairpin Inhibitors are also commercially available and can be obtained from Thermo Scientific. These inhibitors can include chemical modifications and secondary structure motifs. In some embodiments, secondary structural elements can be identified that can enhance the potency of an anti-miR-135a molecule (see e.g., US2006/0223777). Other such improvements in antagomir design are also contemplated for use in the disclosed methods.

Downstream Inhibitors of miR-135a Pathway: In some embodiments, the inhibitor of the miR-135a pathway described herein targets a downstream effector of the miR-135a pathway (e.g., adenomatous polyposis coli gene (APC)). Inhibitors of the miR-135a pathway can be e.g., a small molecule, an RNA interference molecule, or an antibody.

As used herein, the term "small molecule" refers to a chemical agent including, but not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Small molecules agents can be identified from within a small molecule library, which can be obtained from commercial sources such as AMRI (Albany, N.Y.), AsisChem Inc. (Cambridge, Mass.), TimTec (Newark, Del.), among others, or from libraries as known in the art.

Antibodies can be used to inhibit tumor growth by e.g., recognition of an epitope such that a bound antibody inhibits cell growth, proliferation or tumor growth by e g., inhibiting miR-135a or a downstream molecule thereof, such as APC. Production of antibodies useful for the methods described herein are known to those of skill in the art and are described in e.g., Harlow & Lane, Antibodies, A Laboratory Manual (CSHP NY, 1988, which is herein incorporated by reference in its entirety).

RNA interference agents can be used with the methods described herein, to treat a taxane-resistant cancer or inhibit miR-135 pathway activity in a tissue or tumor. "RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B., *J. of Virology* 76(18):9225 (2002), herein incorporated by reference in its entirety), thereby inhibiting expression of the target gene.

As used herein, "inhibition of target gene expression" includes any decrease in expression (e.g., miRNA or mRNA expression, protein expression) or protein activity or level of the target gene or protein encoded by the target gene as compared to a situation wherein no RNA interference has been induced. The decrease can be of at least 20%, 30%, 40%, 50%, 60%, 70%, 80%, 90%, 95% or 99% or more as compared to the expression of a target gene or the activity or level of the protein encoded by a target gene which has not been targeted by an RNA interfering agent. RNA interfering agents contemplated for use with the methods described herein include, but are not limited to, siRNA, shRNA, miRNA, and dsRNAi.

Pharmaceutically Acceptable Carriers

Subjects determined to have a taxane-resistant cancer can be treated with therapeutic compositions that inhibit the miR-135a pathway and a taxane as described herein. Such therapeutic compositions contain a physiologically tolerable carrier together with an active agent as described herein, dissolved or dispersed therein as an active ingredient. In a preferred embodiment, the therapeutic composition is not immunogenic when administered to a mammal or human patient for therapeutic purposes. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein.

Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques.

Delivery of Nucleic Acid Based Inhibitors

In general, any method of delivering a nucleic acid molecule can be adapted for use with an antagomir, an RNAi interference (RNAi) molecule, or an oligonucleotide for inhibiting a member of the miR-135a pathway (see e.g., Akhtar S. and Julian R L. (1992) *Trends Cell. Biol.* 2(5): 139-144; WO94/02595, which are incorporated herein by reference in their entirety). The non-specific effects of an antagomir or RNAi molecule can be minimized by local administration by e.g., direct injection into a tissue including, for example, a tumor or topically administering the molecule. Local administration of a nucleic acid molecule to a tumor limits the exposure of the nucleic acid to systemic tissues and permits a lower dose of the nucleic acid molecule to be administered.

For administering a nucleic acid (e.g., an antagomir of miR-135a) systemically for the treatment of a taxane-resistant cancer, the nucleic acid molecule can either be modified or alternatively delivered using a drug delivery system; both methods act to prevent the rapid degradation of the nucleic acid molecule by endo- and exo-nucleases in vivo. Modification of the nucleic acid molecule or the pharmaceutical carrier can also permit targeting of the nucleic acid to the target tissue and avoidance of undesirable off-target effects.

In an alternative embodiment, the nucleic acid molecules can be delivered using drug delivery systems such as e.g., a nanoparticle, a dendrimer, a polymer, liposomes, or a cationic delivery system. Positively charged cationic delivery systems facilitate binding of an nucleic acid molecule (negatively charged) and also enhance interactions at the negatively charged cell membrane to permit efficient uptake of a nucleic acid by the cell. Cationic lipids, dendrimers, or polymers can either be bound to a nucleic acid molecule, or induced to form a vesicle or micelle (see e.g., Kim S H., et al (2008) *Journal of Controlled Release* 129(2):107-116) that encases a nucleic acid molecule. The formation of vesicles or micelles further prevents degradation of the nucleic acid molecule when administered systemically. Methods for making and administering cationic-RNAi complexes are well within the abilities of one skilled in the art (see e.g., Sorensen, D R., et al (2003) J. Mol. Biol 327:761-766; Verma, U N., et al (2003) Clin. Cancer Res. 9:1291-1300; Arnold, A S et al (2007) J. Hypertens. 25:197-205, which are incorporated herein by reference in their entirety).

Some non-limiting examples of drug delivery systems useful for systemic administration of nucleic acids include DOTAP (Sorensen, D R., et al (2003); Verma, U N., et al (2003)), Oligofectamine, "solid nucleic acid lipid particles" (Zimmermann, T S., et al (2006) *Nature* 441:111-114), cardiolipin (Chien, P Y., et al (2005) *Cancer Gene Ther.* 12:321-328; Pal, A., et al (2005) *Int J. Oncol.* 26:1087-

1091), polyethyleneimine (Bonnet M E., et al (2008) *Pharm. Res.* 25(12):2972-82; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A., et al (2007) *Biochem. Soc. Trans.* 35:61-67; Yoo, H., et al (1999) *Pharm. Res.* 16:1799-1804).

In another embodiment, single-stranded miRNA inhibitors can be expressed from transcription units within cells using eukaryotic promoters in appropriate DNA/RNA vectors. Suitable vectors include, but are not limited to, DNA plasmids and viral vectors. Such viral vectors include, but are not limited to, adeno-associated virus, retrovirus, adenovirus, lentivirus, or alphavirus. In another embodiment, pol III based constructs can be used to express inhibitory nucleic acid molecules (U.S. Pat. Nos. 5,902,880 and 6,146,886). Viral vectors capable of producing either persistent or transient expression of miRNA antagonists in cells can be used.

In some embodiments, the miR-145a pathway inhibitor is administered using a controlled or sustained release system. Controlled or sustained release can be achieved by the addition of time-release additives, such as polymeric structures, matrices, that are known in the art. Such inserts, transdermal patches, bandages or articles can be used to deliver a miRNA inhibitor and can comprise a mixture or coating of polymers that provide release of the active agents at a constant rate over a prolonged period of time.

In some embodiments, a miRNA inhibitor can be administered using electroporation. For example, the nucleic acids are administered to the skin and a pulsed electric field applied to the skin to cause electrotransport of the nucleic acid inhibitors into cells of the skin (see e.g. U.S. Pat. No. 6,520,950, among others). Electroporation can also be used to direct delivery of an miRNA inhibitor to a tumor.

Combination Treatments and Additional Chemotherapeutic Agents

The methods provided herein for treating a taxane-resistant cancer can be combined with other therapies useful in the treatment of taxane-resistant cancer. For example, elevated prohibitin levels have been shown to play a role in taxane-resistant cancers, and inhibition of prohibitin can reduce taxane-resistance (see e.g., US2009/0312405, which is incorporated herein by reference in its entirety). Thus, any method for inhibiting prohibitin (e.g., US2009/0312405) can be used in combination with an inhibitor of miR-135a in the treatment of a taxane-resistant cancer. Administration of a prohibitin inhibitor can occur before, during, or after administration of the miR-135a inhibitor, as described herein. Exemplary inhibitors of prohibitin are known in the art and are described e.g., in US2009/0312405, herein incorporated by reference in its entirety.

In some embodiments, the inhibitor of miR135a is administered in combination with an additional compound or agent that prevents or reverses taxane-resistance including, but not limited to, an inhibitor of glutathione-S-transferase π, or an inhibitor of p-glycoprotein.

In some embodiments, the methods for treating a taxane-resistant cancer (e.g., with a taxane and an inhibitor of the miR-13a pathway) can further include the use of one or more additional anti-cancer or chemotherapeutic agents.

Non-limiting examples of chemotherapeutic agents can include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; chloranbucil; GEMZAR® gemcitabine; 6-thioguanine; mercaptopurine; platinum analogs such as cisplatin, oxaliplatin and carboplatin; vinblastine; platinum; etoposide (VP-16); ifosfamide; mitoxantrone; vincristine; NAVELBINEO. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In addition, the methods of treatment can further include the use of radiation or radiation therapy. Further, the methods of treatment can further include the use of surgical treatments.

Dosage and Administration

In one aspect, the methods described herein provide a method for killing a taxane-resistant cancer cell or for treating a taxane-resistant cancer in a subject. In one embodiment, the subject can be a mammal. In another embodiment, the mammal can be a human, although the approach is effective with respect to all mammals. In one embodiment, the method comprises administering to the subject an effective amount of a pharmaceutical composition comprising an agent that inhibits miR-135a pathway activity, in a pharmaceutically acceptable carrier.

The dosage range for the agent depends upon the potency, and includes amounts large enough to produce the desired effect, e.g., a reduction in miR-135a pathway activity as assessed by determining the expression of miR-135a as described in the Examples section. The dosage should not be so large as to cause unacceptable adverse side effects. Generally, the dosage will vary with the type of agent or inhibitor (e.g., an antibody or fragment, small molecule, siRNA, etc.), and with the age, condition, and sex of the patient. The dosage can be determined by one of skill in the art and can also be adjusted by the individual physician in the event of any complication. Typically, the dosage will range from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 µg/kg body weight to 30 µg/kg body weight. Alternatively, the dose range will be titrated to maintain serum levels between 5 µg/mL and 30 µg/mL.

In some embodiments, a miRNA inhibitor (e.g., a nucleic acid inhibitor) can be administered at a unit dose less than about 75 mg per kg of bodyweight, or less than about 70, less than about 60, less than about 50, less than about 40, less than about 30, less than about 20, less than about 10, less than about 5, less than about 2, less than about 1, less than about 0.5, less than about 0.1, less than about 0.05, less than about 0.01, less than about 0.005, less than about 0.001, or less than about 0.0005 mg per kg of bodyweight, and less than 200 nmol of miRNA antagonist per kg of bodyweight, or less than 1500, less than 750, less than 300, less than 150, less than 75, less than 15, less than 7.5, less than 1.5, less than 0.75, less than 0.15, less than 0.075, less than 0.015, less than 0.0075, less than 0.0015, less than 0.00075, less than 0.00015 nmol of miRNA antagonist per kg of bodyweight.

Administration of the doses recited above can be repeated for a limited period of time. In some embodiments, the doses are given once a day, or multiple times a day, for example but not limited to three times a day. In a preferred embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

A therapeutically effective amount is an amount of an agent that is sufficient to produce a statistically significant, measurable change in e.g., miR-135a expression and/or activity, APC activity and/or expression, tumor size, tumor volume, tumor growth rate, etc. (see "Efficacy Measurement" below). Such effective amounts can be gauged in clinical trials as well as animal studies for a given inhibitor.

Agents useful in the methods and compositions described herein can be administered topically, intravenously (by bolus or continuous infusion), orally, by inhalation, intraperitoneally, intramuscularly, subcutaneously, intracavity, and can be delivered by peristaltic means, if desired, or by other means known by those skilled in the art. For the treatment of tumors, the agent can be administered systemically, or alternatively, can be administered directly to the tumor e.g., by intratumor injection or by injection into the tumor's primary blood supply.

Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. An agent can be targeted by means of a targeting moiety, such as e.g., an antibody or targeted liposome technology. In some embodiments, an agent or inhibitor can be targeted to tissue- or tumor-specific targets by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. The addition of an antibody to an agent or inhibitor permits the agent attached to accumulate additively at the desired target site. Antibody-based or non-antibody-based targeting moieties can be employed to deliver a ligand or the inhibitor to a target site. Preferably, a natural binding agent for an unregulated or disease associated antigen is used for this purpose.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent injection or other administration. Alternatively, continuous intravenous infusion sufficient to maintain concentrations in the blood in the ranges specified for in vivo therapies are contemplated.

In some embodiments, an inhibitor of the miR-135a pathway and a taxane can be combined with one or more agents such as chemotherapeutic or anti-angiogenic agents, for the treatment of cancer.

In one embodiment, the dose of an agent or inhibitor administered for treatment of a cancer is less than the dose necessary to prevent total mitotic arrest. An appropriate dosage range for in vivo use can be titrated and selected by first determining a dose of agent that completely abolishes mitosis in a particular cell type in culture (i.e., toxic dose). Working below the toxic dose, a therapeutically effective dose can be estimated by assessing e.g., miR-135a pathway activity at a variety of doses. This dosage range can be further titrated in vivo as deemed necessary by one of skill in the art, while taking into account such factors as family history of disease, prognostic markers, and severity of disease.

In some embodiments of the methods described herein, a taxane-resistant cancer is treated with a combination of a miR-135a pathway inhibitor and a taxane compound. In such a combination therapy, an agent (e.g., an miR-135a pathway inhibitor) can be administered before, during, or after commencing therapy with another agent (e.g., a taxane compound), as well as any combination thereof, i.e., before and during, before and after, during and after, or before, during and after commencing the combination therapy. Combination agents can include, for example, an inhibitor of miR-135a, an inhibitor of APC, an inhibitor of HIF1AN, a taxane or an additional chemotherapeutic agent as described herein. Also, in general, the therapeutic agents do not have to be administered in the same pharmaceutical composition, and may, because of different physical and chemical characteristics, have to be administered by different routes. For example, an agent can be administered orally to generate and maintain good blood levels thereof, while another agent can be administered by inhalation, or vice versa. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

Efficacy Measurement

The efficacy of a given treatment for a taxane-resistant cancer can be determined by the skilled clinician. However, a treatment is considered "effective treatment," as the term is used herein, if any one or all of the signs or symptoms of, as but one example, cancer are altered in a beneficial manner, other clinically accepted symptoms or markers of disease are improved, or even ameliorated, e.g., by at least 10% following treatment with an inhibitor. Efficacy can also be measured by failure of an individual to worsen as assessed by hospitalization or need for medical interventions (e.g., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the pathogenic growth of cancer cells; or (2) relieving the disease, e.g., causing regression of symptoms, reducing the size of a tumor; and (3) preventing or reducing the likelihood of the development of a taxane-resistant cancer or a metastatic disease thereof.

An effective amount for the treatment of cancer (e.g., a taxane-resistant cancer) means that amount which, when administered to a mammal in need thereof, is sufficient to result in effective treatment as that term is defined herein, for that disease. Efficacy of an agent can be determined by assessing physical indicators of cancer, such as e.g., tumor size, tumor volume, tumor growth rate, metastatic phenotype, etc.

Systems

Embodiments of the invention also provide for systems (and computer readable media for causing computer systems) to perform a method for diagnosing a taxane-resistant cancer in a subject, or assessing a subject's risk of developing a taxane-resistant cancer.

Embodiments of the invention can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules may perform other functions, thus the modules are not limited to having any particular functions or set of functions.

The computer readable storage media #30 can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (eraseable programmable read only memory), EEPROM (electrically eraseable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable storage media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable storage media on which such instructions are embodied may reside on one or more of the components of either of a system, or a computer readable storage medium as described herein, may be distributed across one or more of such components.

The computer-readable storage media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions can be embodied as any type of computer code (e.g., software or microcode) that can be employed to program a computer to implement aspects of the present invention. The computer executable instructions can be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the invention include at minimum a determination system #40, a storage device #30, a comparison module #80, and a display module #110. The functional modules can be executed on one, or multiple, computers, or by using one, or multiple, computer networks. The determination system has computer executable instructions to provide e.g., expression information in computer readable form.

The determination system #40, can comprise any system for detecting a signal representing the expression of miR-135a or a downstream signaling molecule thereof. Such systems can include microscope data acquisition system, miRNA or RNA expression arrays, RT-PCR etc.

The information determined in the determination system can be read by the storage device #30. As used herein the "storage device" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage devices also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage device is adapted or configured for having recorded thereon values representing information relating to the expression level of miR-135a. Such information may be provided in digital form that can be transmitted and read electronically, e.g., via the Internet, on diskette, via USB (universal serial bus) or via any other suitable mode of communication.

As used herein, "stored" refers to a process for encoding information on the storage device. Those skilled in the art can readily adopt any of the presently known methods for recording information on known media to generate manufactures comprising expression information.

In one embodiment the reference data stored in the storage device to be read by the comparison module is e.g., expression data obtained from a population of subjects that do not have a taxane-resistant cancer.

The "comparison module" #80 can use a variety of available software programs and formats for the comparison operative to compare sequence information data determined in the determination system to reference samples and/or stored reference data. In one embodiment, the comparison module is configured to use pattern recognition techniques to compare information from one or more entries to one or more reference data patterns. The comparison module may be configured using existing commercially-available or freely-available software for comparing patterns, and may be optimized for particular data comparisons that are conducted. The comparison module provides computer readable information related to the expression of miR-135a in a subject.

The comparison module, or any other module of the invention, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

The comparison module provides a computer readable comparison result that can be processed in computer readable form by predefined criteria, or criteria defined by a user, to provide a content based in part on the comparison result that may be stored and output as requested by a user using a display module #110.

The content based on the comparison result, can be an increased expression level of miR-135a compared to a reference indicating the presence of taxane-resistant cancer in a subject. Alternatively, the content based on the comparison result can be the absence of expression of miR-135a or a reduced expression of miR-135a compared to a reference indicating the absence of taxane-resistant cancer in an individual.

In one embodiment of the invention, the content based on the comparison result is displayed on a computer monitor #120. In one embodiment of the invention, the content based on the comparison result is displayed through printable media #130, #140. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces.

The methods described herein therefore provide for systems (and computer readable media for causing computer systems) to perform methods for diagnosing taxane-resistant cancers or assessing risk for developing such a cancers in a subject.

Systems and computer readable media described herein are merely illustrative embodiments of the invention for performing methods of diagnosis in an individual, and are not intended to limit the scope of the invention. Variations of the systems and computer readable media described herein are possible and are intended to fall within the scope of the invention.

The modules of the machine, or those used in the computer readable medium, may assume numerous configurations. For example, function may be provided on a single machine or distributed over multiple machines.

Kits

A kit is any manufacture (e.g., a package or container) comprising at least one reagent, e.g., a probe, for specifically detecting a marker of a taxane-resistant cancer (e.g., miR-135a), the manufacture being promoted, distributed, or sold as a unit for performing the methods or assays described herein. When the kits, and methods described herein are used for diagnosis and/or treatment of a taxane-resistant cancer, the miR-135a detection probes or systems can be selected such that a positive result is obtained in at least about 20%, at least about 40%, at least about 60%, at least about 80%, at least about 90%, at least about 95%, at least about 99% or in 100% of subjects afflicted with a taxane-resistant cancer.

When the expression level of miR-135a is used in the methods and assays described herein, the expression level and/or activity of miR-135a can be compared with the expression level of miR-135a in non-cancerous samples of the same type or to another reference standard as described herein.

The kits described herein include methods for assaying cancer cells in a sample (e.g., an archived tissue sample or a sample obtained from a subject). The kits described herein comprise components useful for assessing the presence of a taxane-resistant cancer (e.g., in a sample such as a subject sample). The kit can comprise one or more reagents capable of detecting the expression level of miR-135a e.g., nucleic acids that bind specifically with miR-135a. Such components or reagents can permit detection of miR-135a expression levels directly using e.g., detectable labels or indirectly e.g., amplification of miR-135a prior to detection. Suitable reagents for binding miR-135a include complementary nucleic acids. For example, the nucleic acid reagents can include oligonucleotides (labeled or non-labeled) fixed to a substrate, labeled oligonucleotides not bound with a substrate, pairs of PCR primers, molecular beacon probes, and the like.

The kits described herein can optionally comprise additional components useful for performing the methods and assays described herein. By way of example, the kit can comprise fluids (e.g., SSC buffer) suitable for annealing complementary nucleic acids or for binding an antibody with a protein with which it specifically binds, one or more sample compartments, an instructional material which describes performance of a method as described herein, a sample of normal cells, a sample of cancer cells, and the like.

A kit of the invention can comprise a reagent useful for determining protein level or protein activity of a marker (e.g., prohibitin, or a downstream molecule of miR-135a such as APC).

In some embodiments, the kits described herein comprise one or more of the following: a probe for detecting miR-135a expression, PCR primers for detecting miR-135 expression, a primer for reverse transcription of miR-135a to cDNA, a DNA polymerase, a reverse transcriptase, an miR-135a inhibitor, an antibody directed against APC, an inhibitor of APC, buffers, solutions, etc.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLES

Described herein are studies using a genomic approach to identify microRNAs associated with paclitaxel resistance in a small panel of cell lines representing various human solid malignancies, which were made paclitaxel-resistant in vitro. Subsequently, the in vivo significance of the most discriminating miRNA was evaluated in a mouse model of paclitaxel resistance.

Example 1 miRNA-135a is Upregulated in Various Paclitaxel-Resistant Cell Lines

An initial screen to identify miRNAs involved in paclitaxel resistance was performed in four cell lines that were made paclitaxel-resistant by continuous exposure to paclitaxel in vitro. The inventors identified 18 miRNAs that were deregulated at least 2-fold in resistant cells compared to the paclitaxel-sensitive parental cells.

TABLE 1

Selected up- and down-regulated miRNAs in paclitaxel-resistant compared to paclitaxel-sensitive cell lines.

| miRNA | Fold change PC-14$^{TXT}$ vs. PC-14 | Fold change MCF-7$^{TAX}$ vs MCF-7 | Fold change MES-SA$^{DX5}$ vs MES-SA | Fold change PC-3$^{TXR}$ vs. PC-3 |
|---|---|---|---|---|
| Hs-miR-29a | 0.67 | 5.69 | 1.18 | 0.6 |
| Hs-miR-136a | 6.38 | 0.35 | 9.11 | 1.26 |
| Hs-miR-708 | 5.11 | 0.46 | 2.15 | 0.89 |
| Hs-miR-363 | 0.2 | 0.97 | 0.78 | 0.94 |
| Hs-miR-126 | 0.22 | 0.93 | 3.21 | 1.72 |
| Hs-miR-27b | 0.56 | 2.2 | 0.12 | 1.08 |
| Hs-let-7g | 0.84 | 1.03 | 7.26 | 0.97 |
| Hs-miR-23b | 0.97 | 1.98 | 0.16 | 0.9 |
| Hs-miR-24 | 1.25 | 1.64 | 0.18 | 0.85 |
| Hs-miR-27a | 1.05 | 1.34 | 0.19 | 0.85 |
| Hs-miR-23a | 1.15 | 1.34 | 0.21 | 0.83 |
| Hs-miR-27b* | 0.52 | 1.7 | 0.21 | 1.57 |
| Hs-miR-199a-5p | 0.83 | 0.84 | 0.22 | 0.82 |
| Hs-miR-138 | 0.91 | 0.91 | 0.23 | 0.84 |
| Hs-miR-200a | 0.78 | 0.8 | 0.77 | 0.13 |
| Hs-miR-200b | 0.54 | 0.94 | 0.78 | 0.16 |
| Hs-miR-148a | 1.17 | 0.86 | 1.4 | 5.15 |
| Hs-miR-429 | 0.96 | 0.87 | 0.81 | 0.21 |

When supervised hierarchical clustering was carried out using the 18 differentially expressed miRNAs, cell lines clustered according to cancer type rather than paclitaxel response (data not shown). As miR-135a was most highly and concordantly upregulated in more than one paclitaxel-resistant cell line, that is, 6.4-fold in P-14$^{TXT}$ cells and 9.1-fold in MES-SA$^{DX5}$ cells, the inventors investigated the role of miR-135a in paclitaxel resistance. Quantitative real-time-polymerase chain reaction (qRT-PCR) examination of miR-135a levels revealed a 1.5-fold upregulation in P-14$^{TXT}$ cells (P<0.029) and a 28-fold upregulation in MES-SA$^{DX5}$ cells (P<0.001), confirming the miRNA array results (FIG. 1). In addition, upregulation of miR-135a was observed in two other paclitaxel-resistant cell lines, i.e. 2-fold in A549$^{1R}$ (P=0.016) cells and 9.2-fold in SKOV$^{TR}$ (P=0.029) cells, indicating that the association between miR-135a and paclitaxel resistance is not cell line-specific (FIG. 1).

Example 2

Sensitivity to Paclitaxel is Modulated by Changes in miR-135a Expression in vitro If paclitaxel resistance is causally related to miR-135a upregulation, then altering miR-135a expression levels will modulate paclitaxel sensitivity. The inventors tested this hypothesis by examining paclitaxel response in paclitaxel-resistant cells transfected with a miR-135a inhibitor. The inventors found this to be true when paclitaxel-resistant MES-SA$^{DX5}$ cells were transfected with a miR-135a inhibitor (antagomir). In this experiment, cell survival was 102.2% in cells transfected with a scrambled, non-targeting miRNA.

In contrast, cell survival was reduced to 62.7% when the same cells were transfected with an miR-135a inhibitor and then treated with paclitaxel (FIG. 2A, P=0.003). A similar result was obtained with A549$^{1R}$ cells (FIG. 2A), where transfection with miR-135 inhibitor resulted in a trend towards increased cell sensitivity (P=0.054). To complement these studies, miR-135a levels were elevated in parental, paclitaxel-sensitive cells, with the expectation that this treatment would result in acquisition of the resistant phenotype. In this experiment (FIG. 2B), only 21.8% cell survival was observed in the MES-SA cells after treatment with 100 nM paclitaxel for 72 h. In contrast, 43.6% of the cells survived paclitaxel treatment after transfection with an miR-135a mimic. Again, as shown in FIG. 2B, a similar trend was observed using the A549 parental cells (P=0.051) in the presence and absence of the miR-135a mimic. Complete dose response curves are provided in FIGS. 9A-9D. Consistent with the above results, when paclitaxel-induced apoptosis was determined by measurement of annexin-positive cells, miR-135a inhibition increased apoptosis in the paclitaxel resistant A549TR cells (FIG. 2C, P<0.001), and transfection with the miR-135a mimic decreased paclitaxel-induced apoptosis in the parental A549 cells (FIG. 2D, P<0.001).

Example 3

Overexpression of miR-135a Leads to APC Downregulation

Figure 3C:
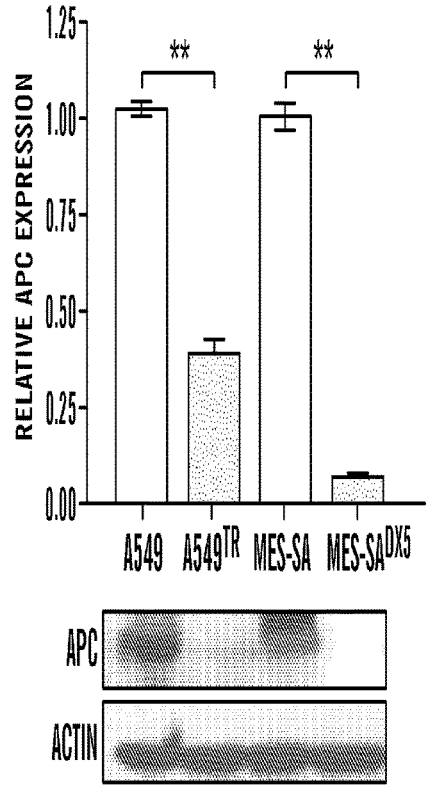
Figure 3D:
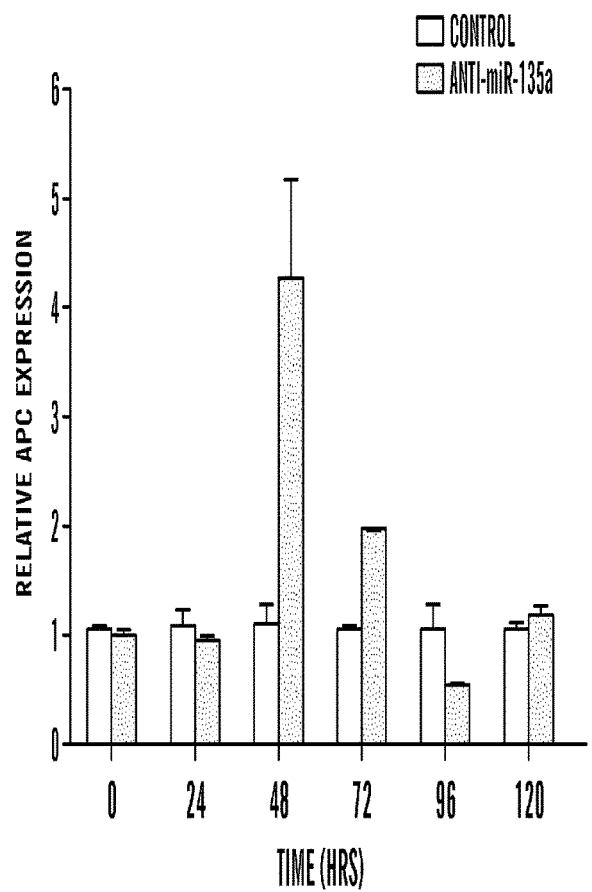
Figure 3E:
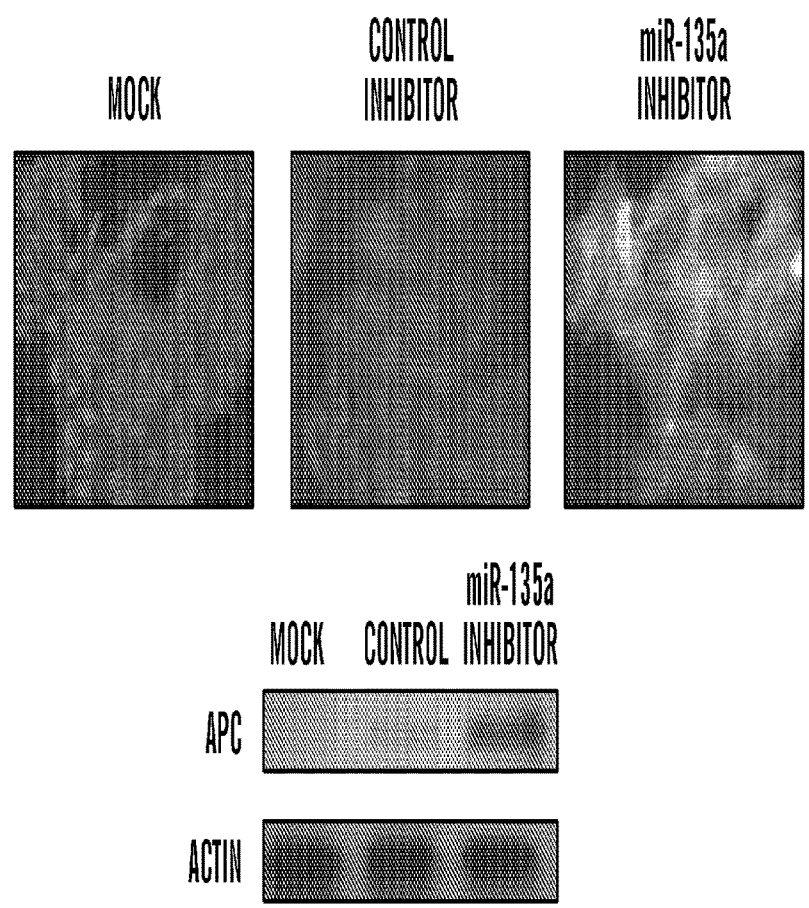

It has been demonstrated that the tumor suppressor adenomatous polyposis coli gene (APC) is regulated by miR-135a (Nagel et al., 2008). The inventors confirmed that miR-135a targeted the 3' untranslated region of APC in both A549 (FIG. 3A) and MES-SA cells (FIG. 3B; P=0.029). To further explore the role of miR-135a upregulation in paclitaxel resistance, APC expression was examined in paclitaxel-sensitive and -resistant cell lines. Analysis of APC mRNA expression levels revealed a 2.6-fold downregulation in A549$^{1R}$ (P<0.001) cells and a 15-fold downregulation in MES-SA$^{DX5}$ (P<0.001) cells. A concordant downregulation of APC was also observed at the protein level (FIG. 3C). Transfection with the anti-miR-135a inhibitor restored APC expression at both the mRNA (FIG. 3D) and protein levels (FIG. 3E).

Example 4 miR-135a-Induced Paclitaxel Resistance is Partly Mediated by APC Downregulation

Figure 4A:
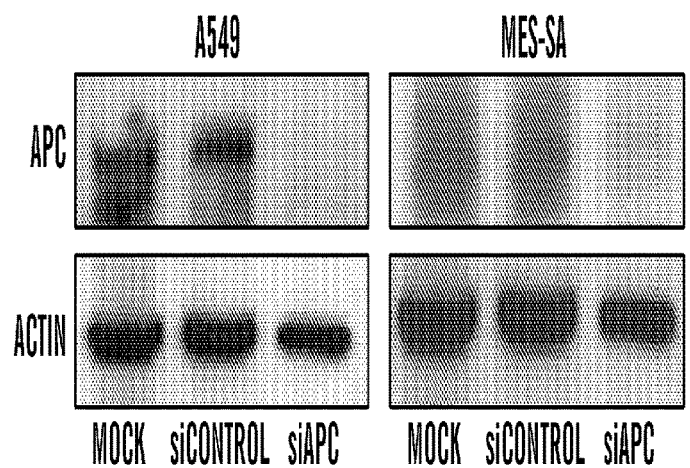
FIGS. 4A-4E are a series of micrographs and line graphs showing that miR-135a-mediated APC suppression contributes to paclitaxel resistance. MES-SA and A549 cells were mock-transfected (mock), transfected with a scrambled siRNA (siControl) or with siRNA directed against APC (siAPC). APC expression was examined by immunoblotting (FIG. 4A). Transfected A549 (FIG. 4B) and MES-SA (FIG. 4C) cells were treated with paclitaxel and viability was assessed using the MTT assay. Values are presented as percentage of cell survival in paclitaxel-treated cells relative to untreated cells. A549 cells stably expressing either non-targeting shRNA (shCON) or shRNA against APC (shAPC) were generated.
Figure 4B:
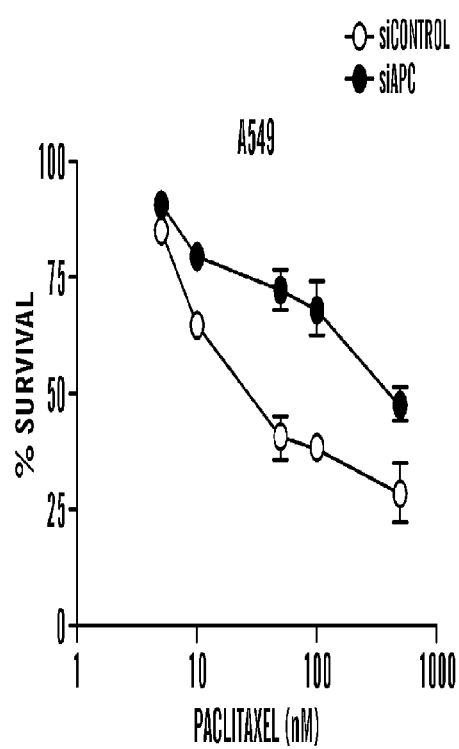
Figure 4C:
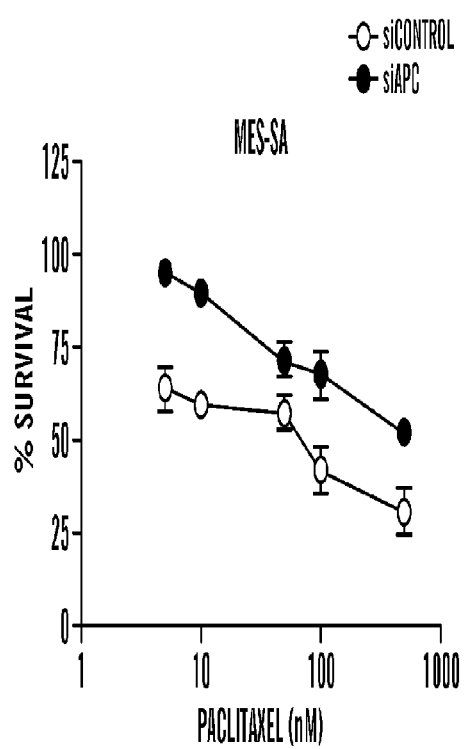
Figure 4D:
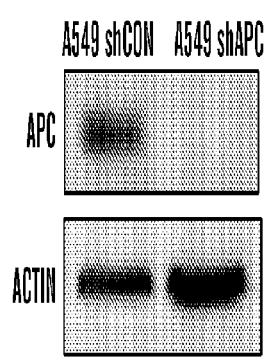
Figure 4E:
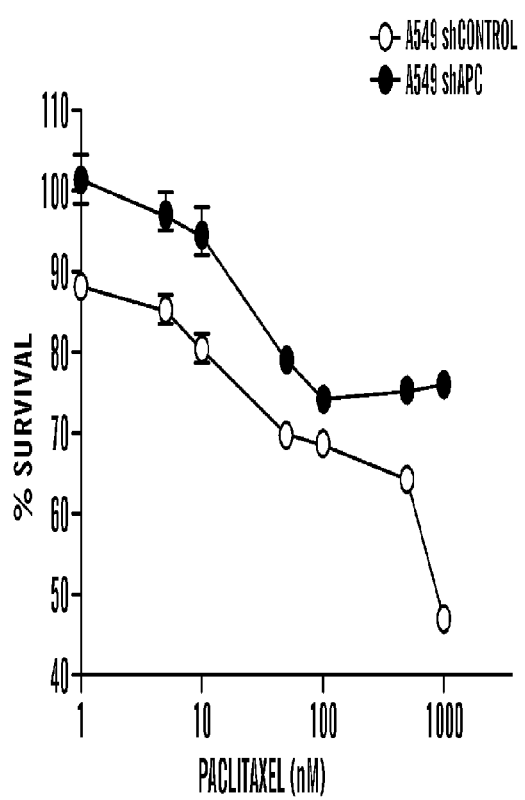

To test the role of APC in cell sensitivity to paclitaxel, APC was suppressed in parental A549 cells and MES-SA cells. Transfection with siRNA against APC completely suppressed APC expression in both cell lines (FIG. 4A) and led to a decrease in paclitaxel-induced cytotoxicity in both cell lines (FIGS. 4B and 4C). Similar results were obtained in A549 cells stably expressing short hairpin RNA against APC (FIGS. 4D and 4E). These results indicate that down-regulation of APC is partly responsible for the effects of miR-135a on paclitaxel sensitivity in these cell lines.

Example 5

The Generation of Paclitaxel-Resistant Cell Lines in vivo

Figure 5A:
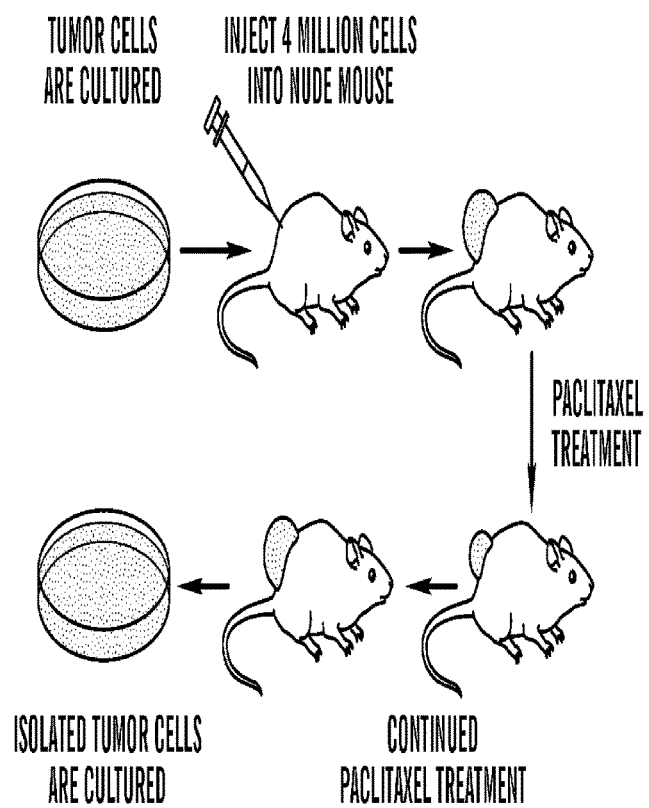
Figures 10A, 10B:
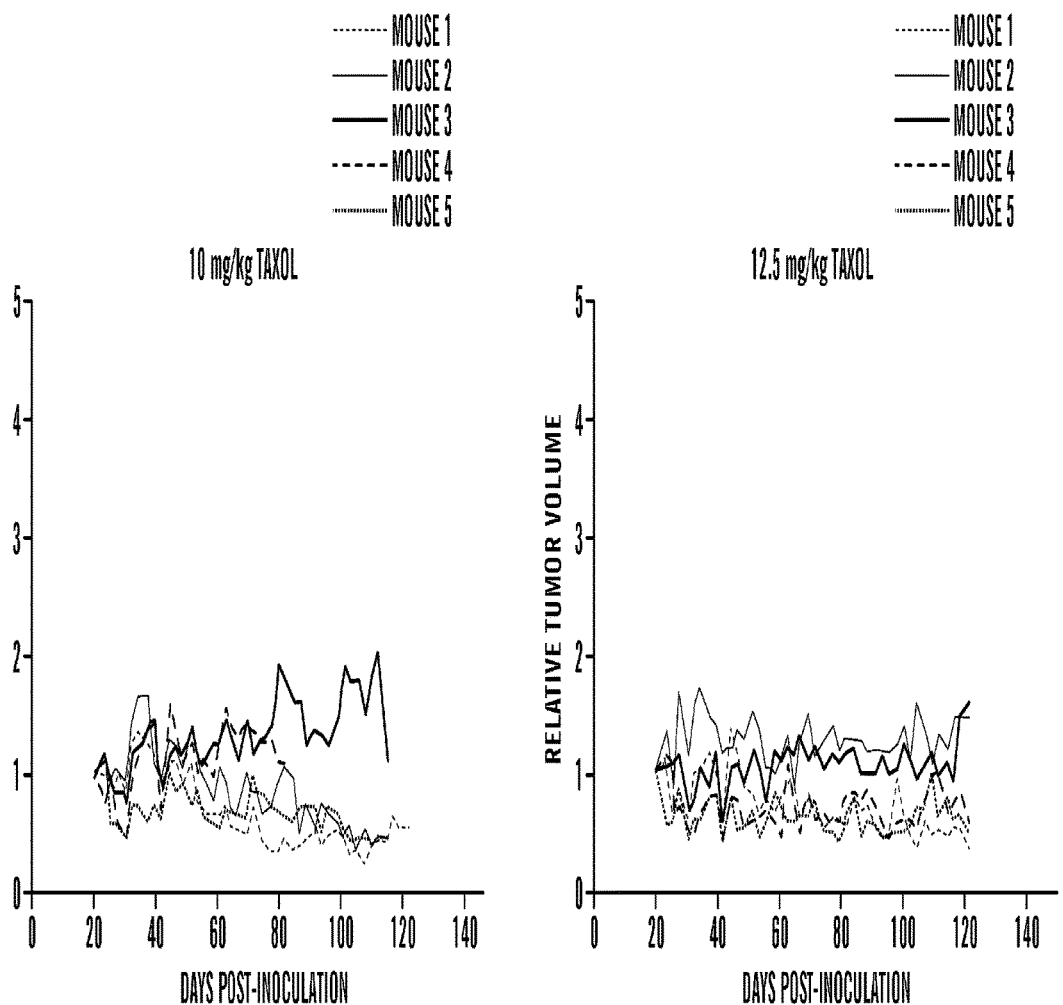
FIGS. 10A-10B are line graphs showing that paclitaxel-resistant tumors do not develop in mice treated with 10 mg/kg or 12.5 mg/kg paclitaxel. Nude mice were inoculated with A549 cells. At an average tumor volume of ~120 mm$^3$, vehicle control and 10 mg/kg (FIG. 10A) or 12.5 mg/kg (FIG. 10B) paclitaxel was administered i.p. every day. Each curve represents the tumor volume on the day of treatment relative to day 0 per mouse.

To further establish the role of miR-135a in paclitaxel response, the A549 xenograft mouse model was adapted from the protocol previously described by Patel et al., 2010. Briefly, nude mice bearing subcutaneous A549 xenografts were injected intraperitoneally with either vehicle or 15 mg/kg paclitaxel until tumors that responded initially began to regrow (FIG. 5A). Representative tumor growth curves for three mice from each group are listed in FIG. 5B. Vehicle-treated tumors show rapid progressive growth. Paclitaxel-treated tumors show two general types of response: 7 out of 10 mice showed prolonged response and 3 out of 10 mice became paclitaxel-refractory, as demonstrated by an increase in tumor volume during continued treatment after initial volume reduction. After 120 days of paclitaxel treatment, control and paclitaxel-refractory tumors were harvested. Within two passages in vitro, RNA was harvested for miRNA evaluation and determination of paclitaxel response. Flow cytometric analysis demonstrated that the harvested cells were composed of human A549 cells and no contaminating mouse cells (data not shown). Cell lines established from paclitaxel-refractory tumors (black bars) were more resistant to paclitaxel in vitro than either parental A549 cells (white bars) or vehicle-treated tumors (striped bars, FIG. 5C). Treatment of xenotransplanted mice with 10 and 12.5 mg/kg paclitaxel did not generate any paclitaxel-refractory tumors (FIGS. 10A-10B).

Example 6

Figures 6A, 6B:
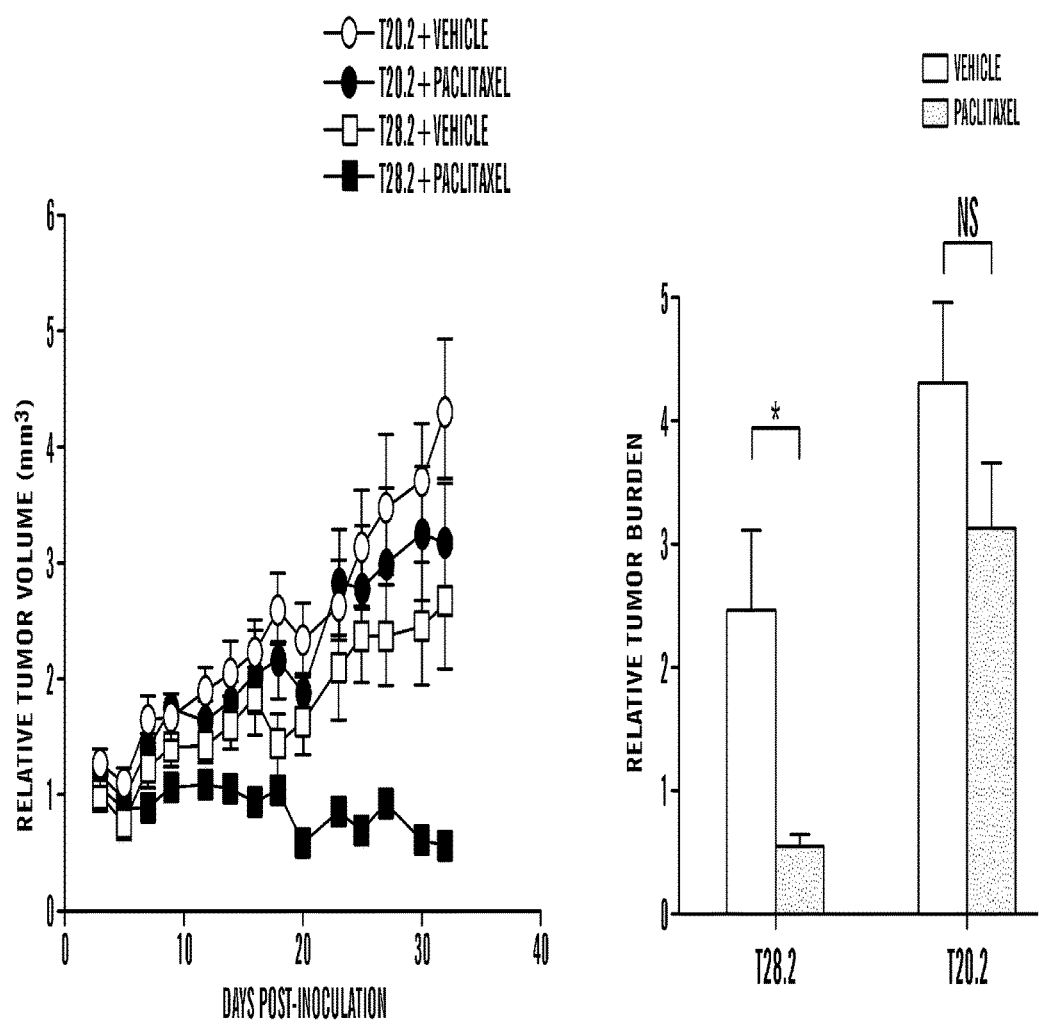
FIGS. 6A-6C are a series of graphs showing data that validate the A549 in vivo paclitaxel resistance model.
Figure 6C:
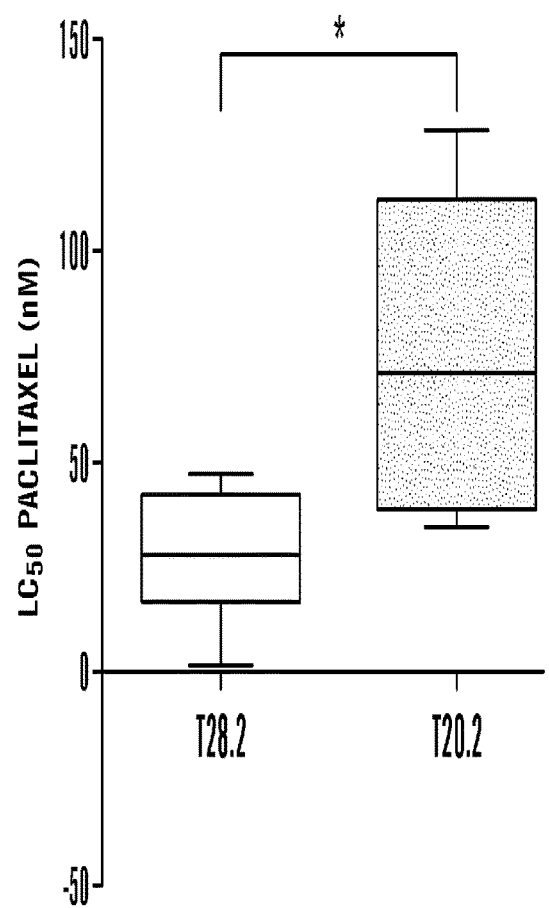

Cells Selected for Paclitaxel Resistance Remain Resistant Upon Retransplantation Tumor clone 20.2 (T20.2), the most paclitaxel-resistant tumor in vitro, was retransplanted into 20 syngeneic mice. Half of these animals were treated with vehicle and half were subjected to another round of i.p. treatment with 15 mg/kg paclitaxel. Tumor clone 28.2 served as a sensitive control in this experiment because: (1) it has a $LC_{50}$ value similar to the parental A549 cells; (2) it is paclitaxel-naïve; and (3) it is similar to T20.2, as both were derived from the same precursor in mice. In the retransplantation, xenografts established from T20.2 showed only a slight delay in tumor growth, whereas xenografts established from the paclitaxel-sensitive control T28.2 shrank substantially after paclitaxel treatment. At the end of the experiment, the relative tumor burden was reduced 4.5-fold in paclitaxel-sensitive control cells (P=0.003) but only 1.4-fold in mice bearing T20.2 xenografts (FIG. 6B). The decreased paclitaxel response of T20.2 compared with T28.2 in mice was associated with a decreased paclitaxel response in vitro (FIG. 6C, P=0.01). The maintenance of paclitaxel resistance upon retransplantation indicates that paclitaxel resistance is associated with stable changes in the tumor rather than in transient changes induced by exposure to the host environment.

Example 7 miR-135a is Upregulated in in vivo Paclitaxel Resistance

In the in vitro experiments described herein, a role was established for miR-135a in the cellular response to paclitaxel. To explore the role of miR-135a expression in vivo, the inventors examined miR-135a expression in three cell lines representing various degrees of paclitaxel resistance.

Figure 7C:
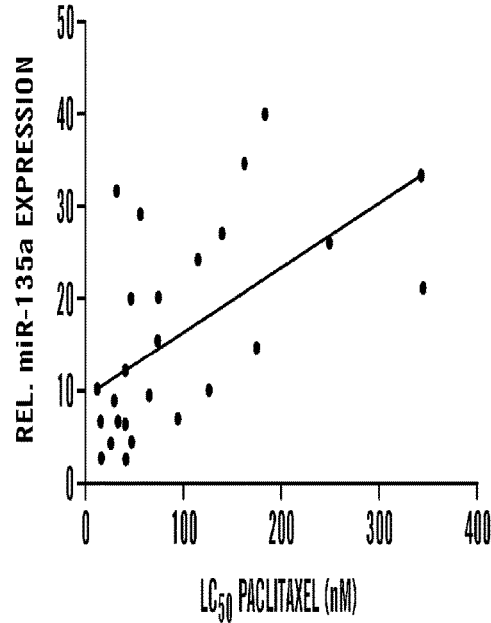
Figure 7D:
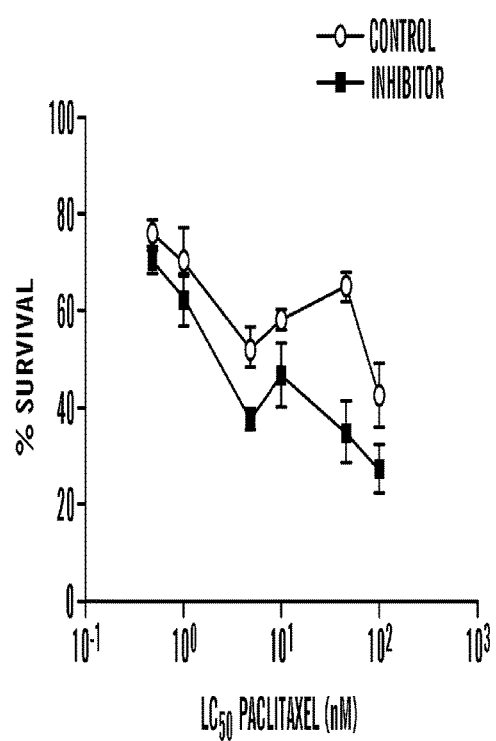
Figure 7E:
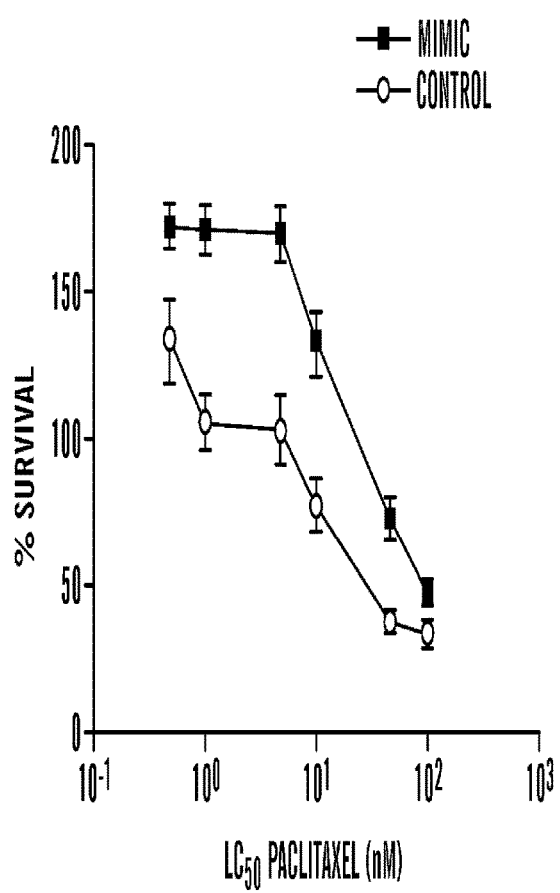

Paclitaxel resistance increased gradually from a median LC50 value of 1.14 nM in the parental A549 cells to 13.27 nM after one in vivo passage (P=0.030) and to 126.6 nM after re-injection (P=0.008, FIG. 7A). As shown in FIG. 7B, decreased paclitaxel response is significantly associated with increased miR-135a expression in tumors selected for paclitaxel resistance in vivo. Cells have a median 1.9-fold higher expression after the initial in vivo passage (round 1) and a 4.1-fold higher expression of miR-135a, compared with the parental A549 cells (P=0.004). The correlation between miR135a expression and paclitaxel response was observed in all cell lines derived from these tumors (FIG. 7C, P<0.001). Transfection with an miR-135a inhibitor modestly increased paclitaxel-induced cytotoxicity in paclitaxel-resistant cells (FIG. 7D). Furthermore, transfection of an miR-135a mimic suppressed paclitaxel-induced cytotoxicity in paclitaxel-sensitive cells (FIG. 7E). Together, these results show that miR135a is involved in the paclitaxel sensitivity of the cell lines established after long-term exposure to paclitaxel in vivo.

Example 8 miR-135a Modulates Tumor Response to Paclitaxel in vivo

Figure 8C:
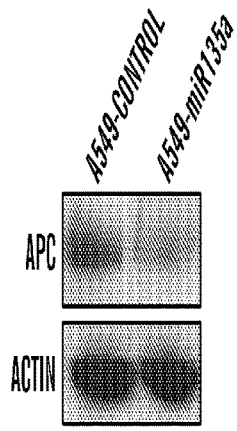
Figure 8D:
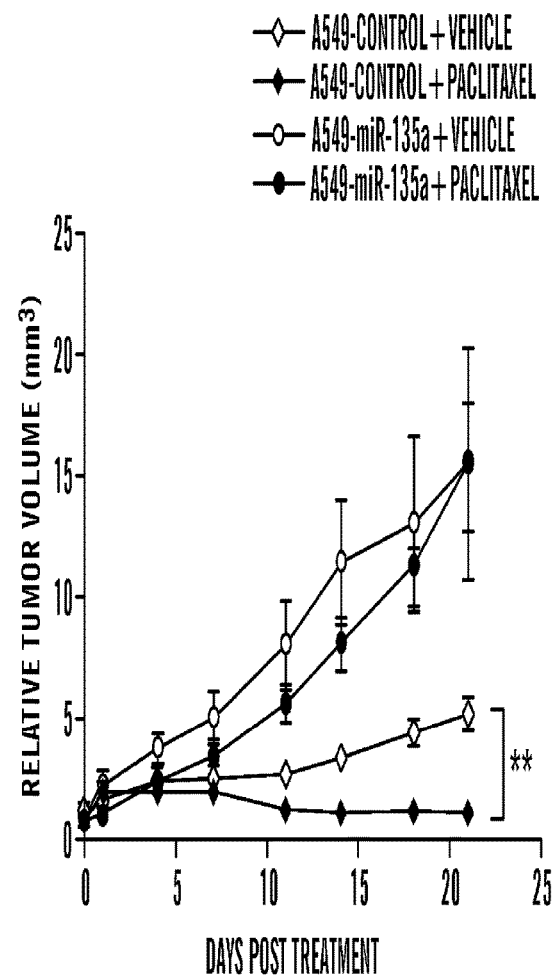
Figure 9A:
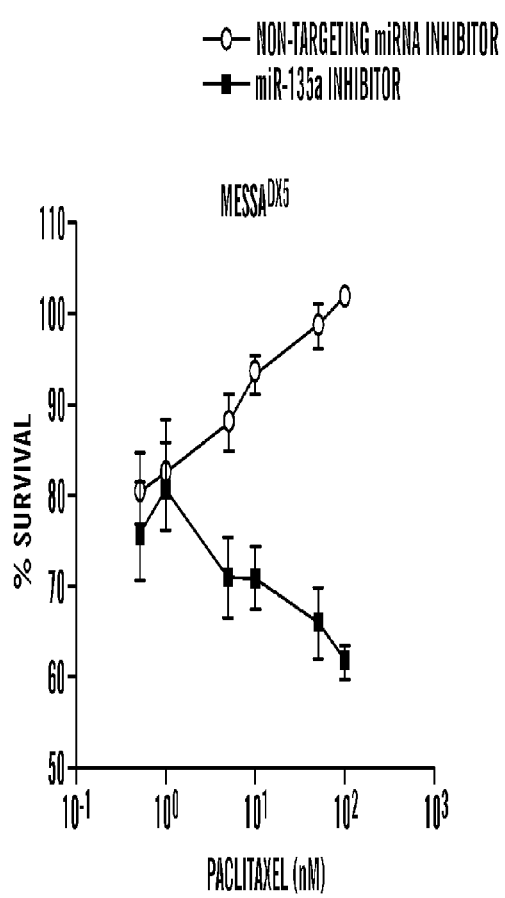
FIGS. 9A-9D are a series of dose response curves showing the function role of miR-135a in paclitaxel resistance. MES-SA$^{DX}$ (FIG. 9A), A549$^{TR}$ cells (FIG. 9B) were transfected with a non-targeting control miRNA or a miR-135a inhibitor and MES-SA (FIG. 9C) or A549 (FIG. 9D) cells with a control or a miR-135a mimic. Post-transfection, cell viability was assessed after exposure to paclitaxel. Shown are the mean and s.e.m. of two independent experiments.
Figure 9B:
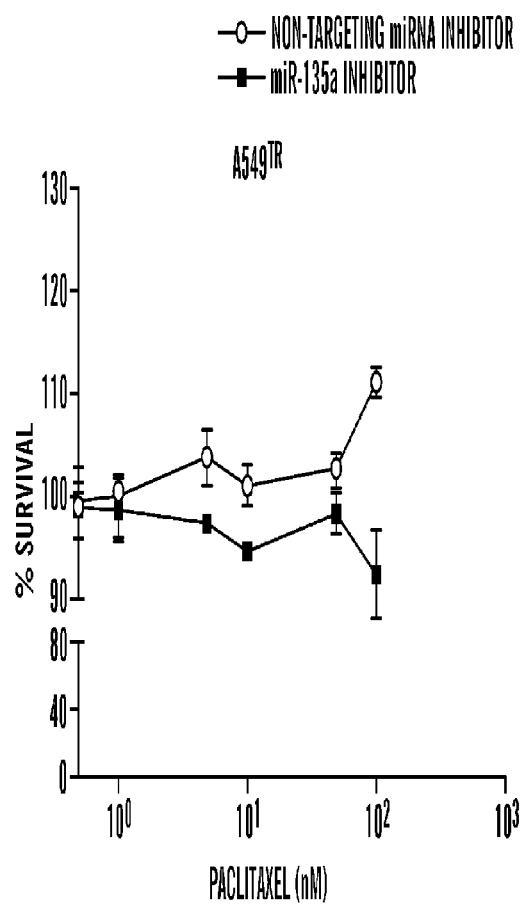
Figure 9C:
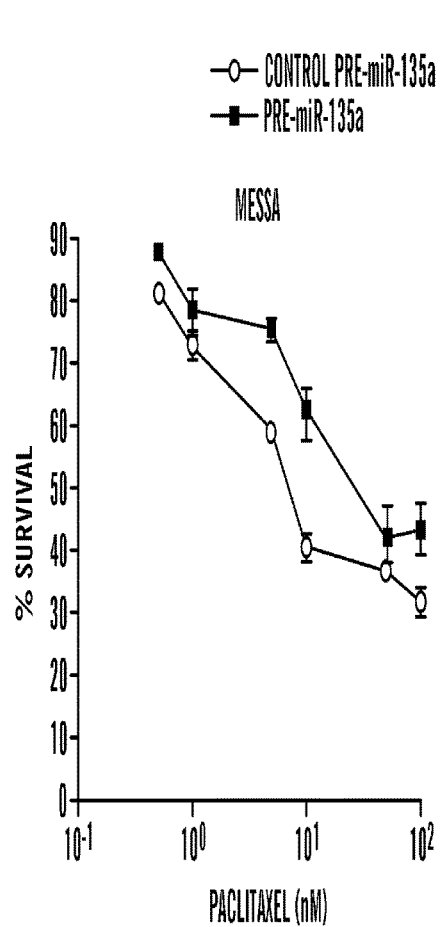
Figure 9D:
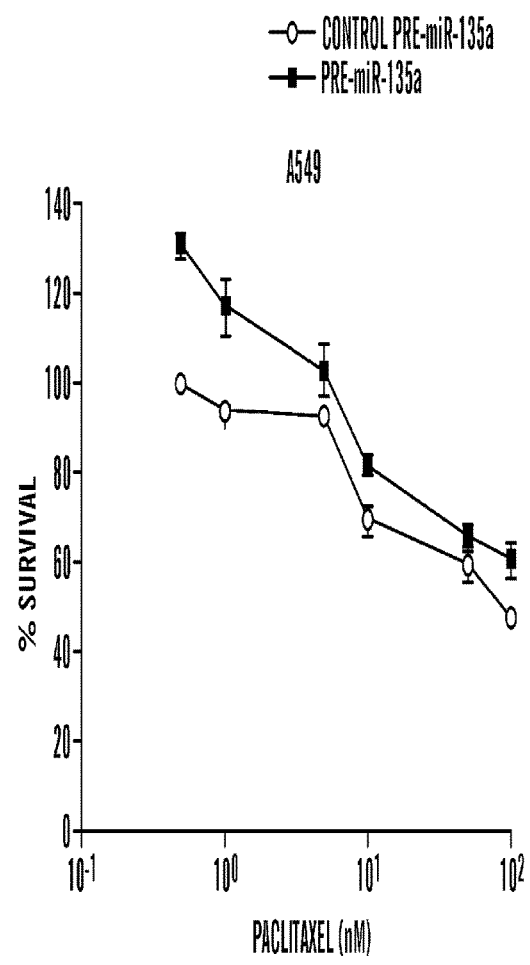

The inventors subsequently investigated the role of miR-135a in paclitaxel sensitivity in vivo. To this aim, A549 cells stably expressing miR-135a were generated, which showed expression of miR-135a approximating that of A549TR cells (P<0.01) (FIG. 8A). As expected, miR-135a knockdown attenuated paclitaxel-induced cell death (FIG. 8B) and APC protein expression (FIG. 8C) relative to control transfected A549 cells in vitro. If overexpression of miR-135a is causally involved in paclitaxel-resistance in vivo, tumors artificially overexpressing miR-135a will show decreased paclitaxel sensitivity. To investigate this hypothesis, A549 control cells and A549 cells stably overexpressing an miR-135a mimic were inoculated subcutaneously into the flanks of nude mice. Paclitaxel treatment was given three times a week for 3 weeks, and tumor size in each group was monitored during the course of treatment. At the end of the experiment, the relative tumor burden was reduced 5-fold in A549 control cells (P<0.001). A549 cells overexpressing miR-135a showed increased cell growth in vivo relative to control untreated cells. In vivo growth of miR-135a overexpressing cells was not reduced by paclitaxel exposure (FIG. 8D). This result demonstrates that miR-135a overexpression alone induces taxane resistance that is maintained during tumor growth in vivo.

Example 9

Summary

Despite their widespread use, the clinical effectiveness of taxanes is limited by the emergence of taxane-resistant cancer cells. This necessitates investigation into the mechanisms of paclitaxel resistance. The current knowledge of the mechanisms underlying paclitaxel resistance is largely derived from in vitro models where resistance is induced by repeated or prolonged exposure of cultured cells to gradually increasing drug concentrations. Although this methodology has imparted important knowledge, it has potential disadvantages. First, cells in solid tumors in vivo tend to be more drug-resistant than the same cells grown in a monolayer in vitro (Hoffman, 1991; Kobayashi et al., 1993). This can be explained by various factors, including decreased drug penetration, quiescence of cells in deeper layers due to cell contact inhibition and hypoxia, or resistance arising from an adaptive, reciprocal signaling between tumor cells and the surrounding microenvironment (Meads et al., 2009; Pollard, 2004). Second, treatment in culture bears little resemblance to in vivo pharmacokinetics and does not allow the formation of active metabolites that may be produced by metabolic activity. Third, the in vitro situation does not address the role of the tumor microenvironment in the generation of drug resistance. To confirm the role of miRNA-135a in paclitaxel resistance, the inventors established a new in vivo mouse model of paclitaxel resistance.

Various methods have been used to study mechanisms of drug resistance in vivo. Generally, mice are implanted with cell lines that were made resistant in vitro. Although the role of drug-resistant genes can be studied this way in vivo (Patel et al., 2010), drug resistance itself is still induced in a monolayer and is associated with the same drawbacks as in vitro drug resistance models. An alternative approach is the use of mice that develop spontaneous tumors as a consequence of conditional tissue-specific mutations in proto-oncogenes and tumor suppressor genes. Using this approach, Rottenberg et al. generated docetaxel-resistant Brca1$^{-/-}$; p53$^{-/-}$ mammary tumors (Rottenberg et al., 2007). In their study, tumors that responded to paclitaxel were allowed to grow back to original size before treatment was resumed. In the present model, a constant 3× weekly treatment schedule was employed, consistent with current clinical practice.

Similar approaches have been employed by others to establish drug-resistant cell lines (Okugawa et al., 2004; Starling et al., 1990; Teicher et al., 1990). Interestingly, contrary to the present model, resistance was not maintained when the established cell lines were exposed to paclitaxel in vitro in these models. The authors suggested that drug resistance of in vivo established cell lines may be dependent on an interaction between the tumor and the host stromal tissues rather than changes at the cellular level. The maintenance of drug resistance in vitro in the present model could be explained by the selection method. Both Okugawa and Teicher et al. retransplanted cells in a new recipient mouse after a single drug dose. This procedure was repeated 6 and 10 times in a 6-month period, respectively. Starling's mice were treated 7 times in 8 weeks with a treatment-free interval of 3 weeks between the first and second rounds of treatment. The 3× weekly schedule for 42 weeks, as used herein, is associated with a prolonged and continuous selective pressure. Cancer cells are notoriously genetically unstable. It has been proposed that acquired drug resistance arises in a step-wise fashion as a consequence of random mutations in tumor subclones (Goldie and Coldman, 1979). Some of these mutations will, by chance, result in an increased survival to the drug being used, causing this subclone to be selected during therapy. Resistance at the cellular level, without the necessity of signals from the microenvironment, may occur at a later stage in the development of resistance, explaining the maintenance of paclitaxel resistance ex vivo in the present model. Since clinical paclitaxel resistance usually takes several months to develop, the present model may be useful in elucidating mechanisms of paclitaxel resistance.

miR-135a is a member of the miR-135 subfamily, which is comprised of miR-135a and miR-135b. The inventors' current work demonstrates that upregulation of miR-135a correlates with the acquisition of taxane resistance in cells selected for resistance either in vitro or in vivo. Manipulation of miR-135a levels has a functional effect on taxane sensitivity in these lines. The results described herein indicate that suppression of miR-135a is a reasonable approach to improving or prolonging drug sensitivity.

A recent report showed that the tumor suppressor gene APC is targeted by the miR-135a family (Nagel et al., 2008). The data described herein confirm that APC is an miR-135a target and implicates miR-135a-mediated APC downregulation as a mechanism for miR-135a-induced taxane resistance. The best-known function of the APC protein is the regulation of the Wnt signaling cascade through downregulation of β-catenin (Giles et al., 2003). Loss of APC expression leads to nuclear accumulation of b-catenin and inappropriate activation of its target genes (Giles et al., 2003), including the growth-promoting genes c-myc and cyclin-D 1 and the anti-apoptotic gene survivin (Zhang et al., 2001). Collectively, these changes can lead to reduced paclitaxel-induced apoptosis (Dikovskaya et al., 2007). In addition, defects in the mitotic checkpoint function have been associated with reduced paclitaxel-induced apoptosis (Anand et al., 2003; Sudo et al., 2004). APC regulates the mitotic checkpoint by binding to microtubules during mitosis (Fodde et al., 2001) and interacting with kinetochore-associated proteins (Kaplan et al., 2001; Aoki and Taketo, 2007). Consequently, knockdown of APC by miR-135a may contribute to paclitaxel resistance by decreasing apoptosis, directly or indirectly by interfering with the mitotic spindle checkpoint.

A recent report showed that treatment with the angiogenesis inhibitor endostatin significantly improved the antitumor efficacy of paclitaxel in Lewis lung cell carcinoma (Huang and Chen, 2010). This implicates increased angiogenesis in paclitaxel resistance. Hypoxia-inducible factor 1 (HIF-1) is the key regulator of oxygen homeostasis that controls angiogenesis, erythropoiesis and glycolysis through transcriptional activation of target genes under hypoxic conditions (Fong, 2008). Hypoxia-inducible factor 1-alpha inhibitor (HIF1AN) is a protein that binds to HIF-1a and inhibits its transcriptional activity (Mahon et al., 2001). HIF1AN is a potential miR-135a target listed in both the TargetScan and PicTar databases and as such HIF1AN can be targeted as described herein for treatment of a taxane-resistant cancer.

The role in paclitaxel resistance proposed herein for miR-135a indicates that clinical taxane resistance can be reversed by inhibiting miR-135a and/or its deregulated downstream pathways. The use of anti-miRs as a therapeutic tool was demonstrated in a recent study, where intratumoral injection of anti-miR-221/222 led to a reduction in tumor growth in a subcutaneous prostate cancer xenograft tumor model (Mercatelli et al., 2008). In addition, several small-molecule antagonists capable of disrupting APC have been identified (Lepourcelet et al., 2004) and represent potential alternatives to genetic manipulation.

In conclusion, the data described herein demonstrate that miR-135a is involved in paclitaxel resistance, both in vitro and in vivo. In addition, the data show that miR-135a-mediated paclitaxel resistance is, in part, mediated by downregulation of APC. The in vivo model described herein represents a promising new paradigm to elucidate mechanisms of paclitaxel resistance. Future genomic or proteomic profiling of the paclitaxel-resistant cell clones generated in this model is likely to generate important new insights into the mechanisms of paclitaxel resistance.

Example 10

Materials and Methods

Cell lines: The human NSCLC line A549 and its paclitaxel-resistant derivative cell lines were described previously (Patel et al., 2010). The human non-small cell lung cancer cell line (NSCLC) PC-14 and its docetaxel-resistant cell line PC-14/TXT were provided by Dr. Nagahiro Saijo (National Cancer Center Research Institute, Tokyo, Japan), the human breast cancer cell line MCF-7 and the multidrug-resistant derivative MCF-7$^{TAX}$ by Dr. Amadeo Parissenti (Laurentian University, Sudbury, ON, Canada) (Villeneuve et al., 2006), the human prostate cancer cell line PC-3 and the paclitaxel resistant variant PC-3$^{TXR}$ by Dr. Atsushi Mizokami (University of Kanazawa, Japan) (Takeda et al., 2007) and the human ovarian cancer cell line SKOV-3 and the paclitaxel resistant variant SKOV-3$^{TR}$ by Dr. Zhenfeng Duan (Massachusetts General Hospital, Boston, Mass.). Multidrug resistant human uterine sarcoma cells MES-SA$^{DX5}$ were purchased at ATCC (Manassas, Va.). All cells were cultured at 37° C. in a humidified atmosphere with 5% $CO_2$ in media supplemented with 10% fetal bovine serum and 1% penicillin/streptomycin (Life Technologies, USA). Media and paclitaxel (Cytoskeleton, USA) concentrations used are specified in Table 2.

TABLE 2

Media and paclitaxel concentrations used in cell culture

| Cell line | Medium | Concentration paclitaxel (nM) |
|---|---|---|
| PC-14 | RPMI-1640 medium | — |
| PC-14$^{TXT}$ | RPMI-1640 medium | — |
| A549 | Kaighn's Modification of Ham's F-12K medium | — |
| A549$^{TR}$ | Kaighn's Modification of Ham's F-12K medium | 100 |
| MES-SA | McCoy's 5A medium | — |
| MES-SA$^{DX5}$ | McCoy's 5A medium | 100 |
| MCF-7 | Dulbecco's Modified Eagle's medium | — |
| MCF-7$^{TAX}$ | Dulbecco's Modified Eagle's medium | 6.6 |
| PC-3 | RPMI-1640 medium | — |
| PC-3$^{TXR}$ | RPMI-1640 medium | 10 |
| SKOV-3 | RPMI-1640 medium | — |
| SKOV-3$^{TR}$ | RPMI-1640 medium | — |

RNA Purification, Labeling and Hybridization

Cells were harvested in log-phase growth and total RNA was extracted using TRIzol Reagent™ (Invitrogen, Carlsbad, Calif.) according to the manufacturer's protocol with an additional extraction with phenol:chloroform:isoamyl alcohol 25:24:1. RNA integrity was assessed with an Agilent Bioanalyser 2100 (Agilent, Palo Alto, Calif.). Two µg of total RNA were labeled using the miRCURY™ Hy3™/Hy5™ labeling kit and hybridized on the miRCURY™ LNA Array v.11.0 (Exiqon, Vedbaek, Denmark) according to the manufacturer's protocol. A common reference pool was constructed using RNA from all samples. Hybridization of the Hy5-labeled pool to each array facilitates comparison of ratios across datasets (Yang and Speed, 2002).

Processing of Microarray Data

Arrays were scanned using a laser confocal scanner (Agilent) and Hy3 (cell line), and Hy5 (common reference pool) signal intensities were calculated. Arrays were repeated if control spike-in oligonucleotides did not produce signals within the expected range. In successful arrays, signal intensities were background corrected using the normexp method (Ritchie et al., 2007) with offset value k=10 and normalized using the global Lowess (Locally weighted scatterplot smoothing) regression algorithm (Cleveland, 1979). The LMR value was calculated per miRNA probe set by log 2-transformation of the mean Hy3/Hy5 ratio (MR). The ΔLMR value, i.e. the difference between the LMR values in the parental cells and their paclitaxel-resistant subclone, was subsequently used to calculate the fold change per miRNA using the following formula: $2^{\Delta LMR}$. For subsequent analysis, the inventors used miRNAs that passed the filtering criteria on variation across samples, i.e. LMR>2.0.

Establishment of in vivo Paclitaxel-Resistant Cell Lines

Figure 11:
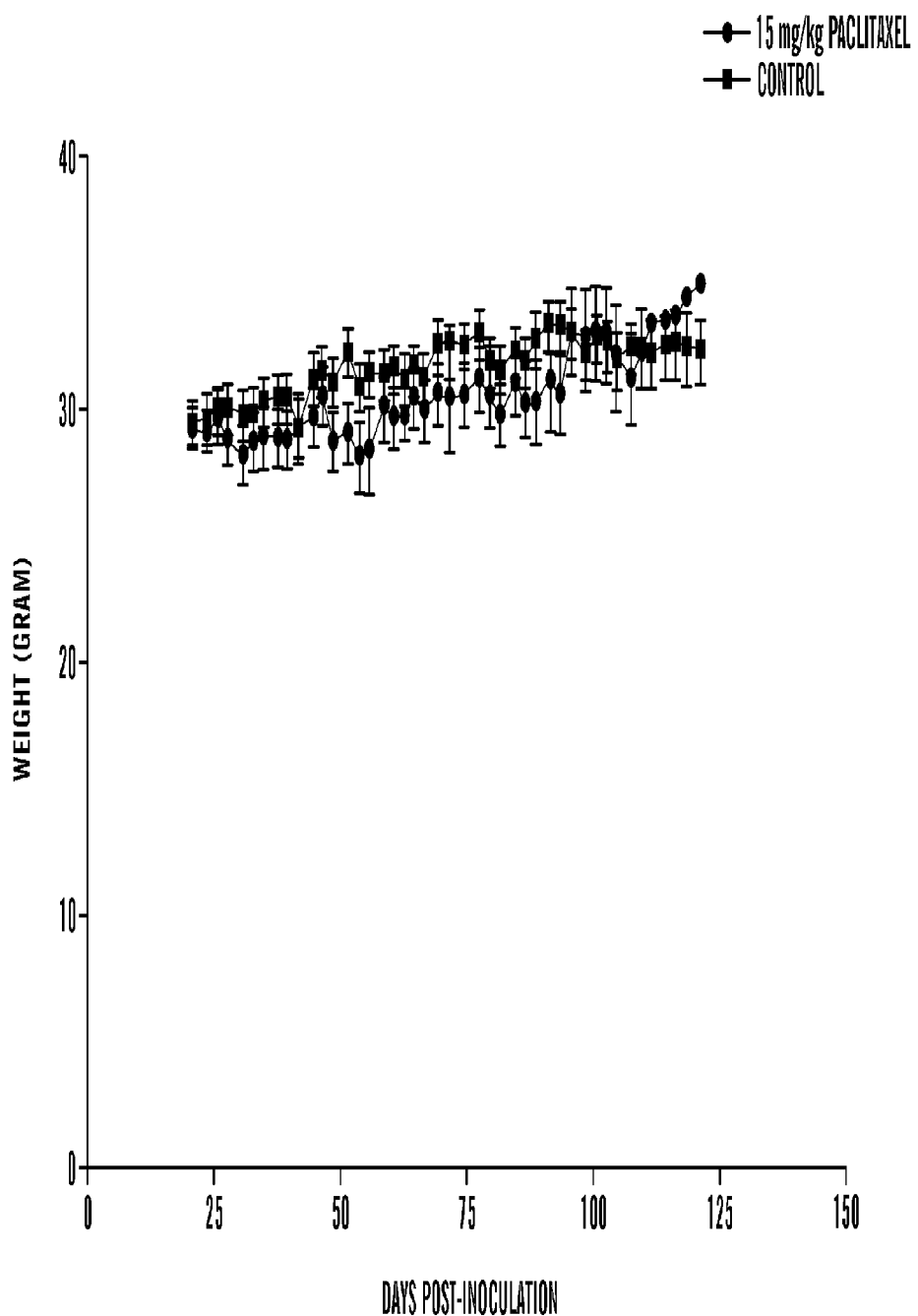
FIG. 11 is a line graph indicating mouse weight in paclitaxel-treated and control groups. Tumor-bearing nude mice were treated i.p. with 15 mg/kg paclitaxel every other day. Animals were weighed before each injection on a digital scale. Each curve represents the mean weight±s.e.m. of 10 mice per day of treatment.
Figure 12:
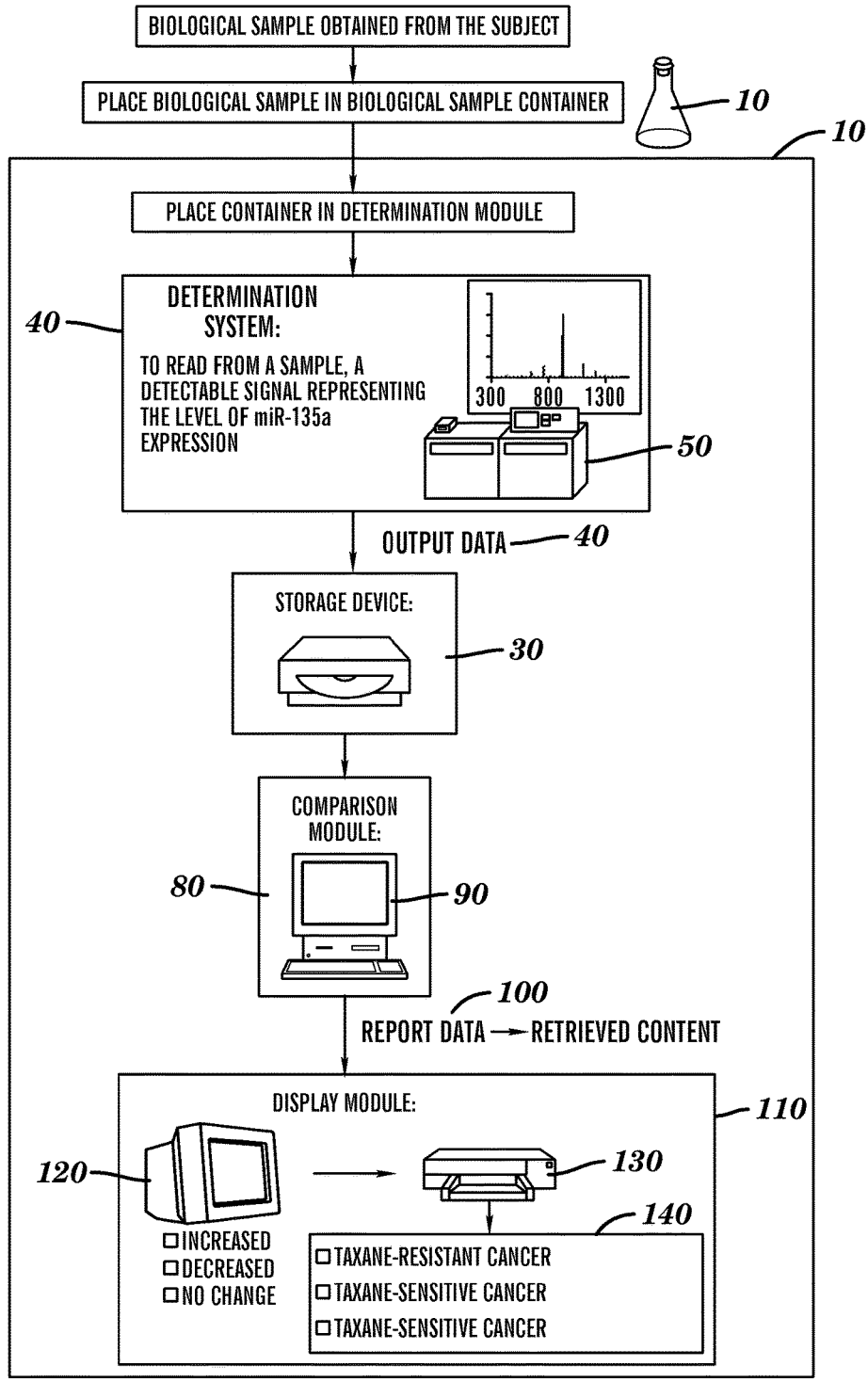
FIG. 12 is a block diagram depicting an exemplary system for use with the diagnostic methods described herein.
Figure 13:
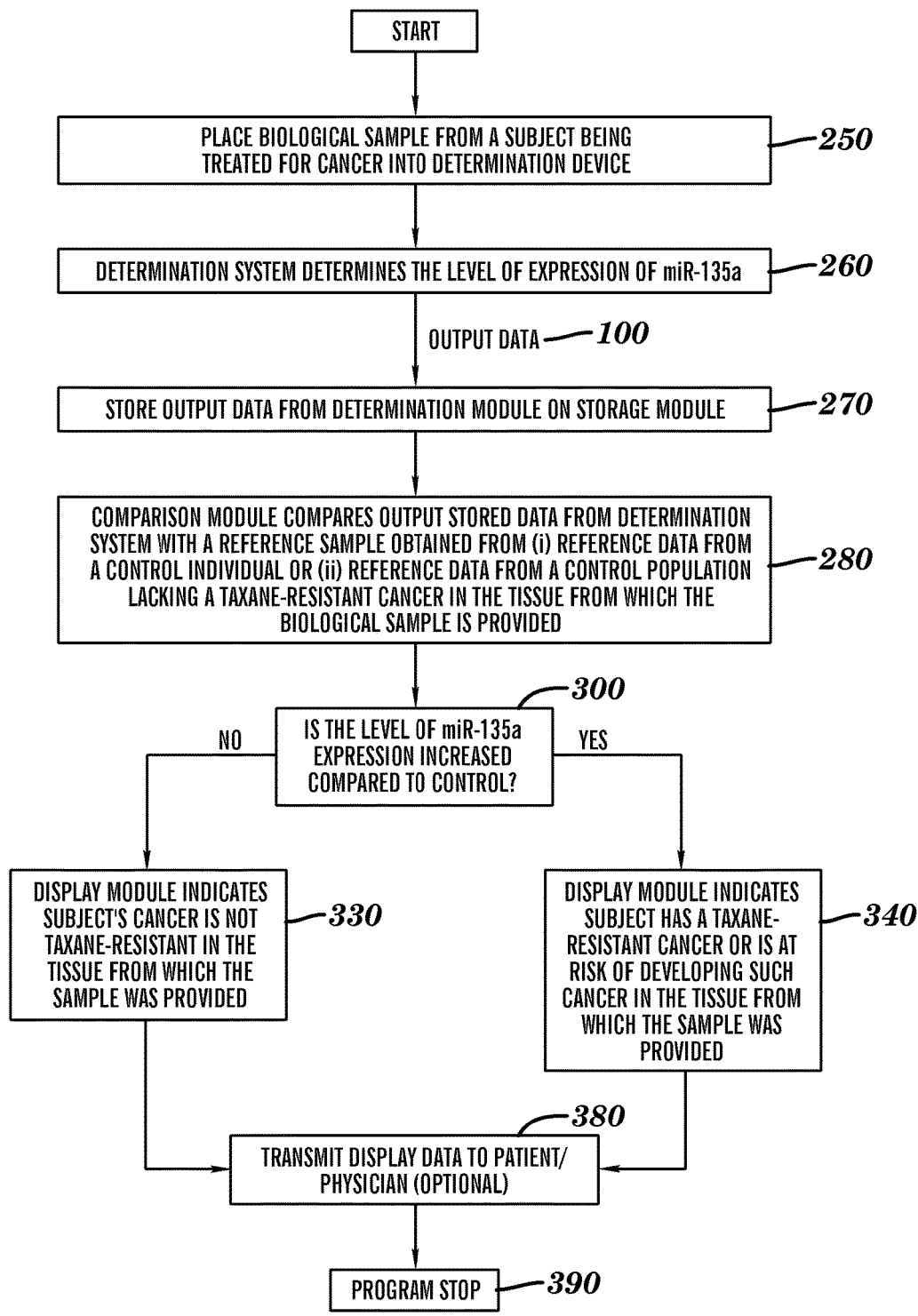
FIG. 13 is a block diagram depicting exemplary instructions encoded on a computer readable storage medium for use with the systems described herein.

Approximately $4 \times 10^6$ human A549 NSCLC cells were resuspended in 50% Matrigel (BD Biosciences, Bedford, Mass.) and injected subcutaneously into the hind flanks of 8-wk old male athymic (nu/nu) nude mice (Taconic Farms, Inc., Hudson, N.Y.). When the average tumor volume reached ~150 mm$^3$, mice (N=10 per group) were randomly assigned to the treatment or control group (Day 0). Mice were treated with vehicle (control) or 15 mg/kg paclitaxel (Bristol-Myers Squibb Co, Princeton, N.J.) intraperitoneally 3 times per week (on Mondays, Wednesdays, and Fridays). This concentration of paclitaxel had minimal effects on mouse morbidity as measured by mouse weight (FIG. 11). Tumor size was determined by digital caliper measurements (length and width in mm), and tumor volume (mm$^3$) was estimated using the formula (length×width$^2$)/2. Effects on tumor growth rate were assessed per mouse by determining the tumor volume on the day of treatment relative to the tumor volume on Day 0. Animals were sacrificed once morbidity became evident or their tumor size exceeded 1000 mm$^3$. Following the indicated treatments, A549 tumors were removed, minced, expanded in vitro without further exposure to paclitaxel and stored in liquid nitrogen. All animal studies were conducted in accordance with the guidelines established by the internal Institutional Animal Care and Use Committee.

Cytotoxicity Assays

Cell growth inhibition was determined by a 3-(4,5-dimethylthiazol-2-yl)-2,5-diphenyltetrazolium (MTT) bromide assay. Briefly, ~2.5×10$^4$ cells were plated in a 96-well plate and paclitaxel was added in appropriate concentrations 24 hours later. An equivalent amount of diluent (DMSO) was added to culture medium as a negative control. After 72 hours of drug incubation, 20 µl of MTT (Sigma Chemicals, St. Louis, Mo.; 20 mg/ml) was added to each well. After incubation for an additional 4 hours, 200 µl of isopropanol-HCl solution was added to each well to dissolve the cell pellets. Absorbance was determined using a 96-well SpectraMax plate reader (Molecular Devices, Sunnyvale, Calif.) at 560 nm and 650 nm (background).

Quantitative Real Time PCR (qRT-PCR)

Total cellular RNA was extracted using Trizol reagent (Invitrogen). In order to quantify APC mRNA expression levels, cDNA was synthesized using the iScript cDNA synthesis kit (Bio-Rad Laboratories, Richmond, Va., USA) and qRT-PCR was carried out using iQ SYBR Green master mix (Bio-Rad). Primer sequences used are: APC, 5'-GGAAGCAGAGAGAAAGT ACTGGA-3' (sense, SEQ ID NO: 1) and 5'-CTGAAGTTGAGCGT AATACCAG-3 ' (antisense, SEQ ID NO: 2), GAPDH, 5'-GTATTGGGCGC-CTGGTCACC-3 ' (sense, SEQ ID NO: 3) and 5'-CGGGAAGATG GTGATGG-3' (antisense, SEQ ID NO: 4). Expression of miR-135a and 5S sRNA as a reference was analyzed by the mirVana™ qRT-PCR miRNA Detection Kit (Ambion/Applied Biosystems, Austin, Tex.) in conjunction with real-time PCR with SYBR Green I (Bio-Rad). All reactions were conducted in triplicate in a LightCycler® 480 Real-Time PCR System (Roche, Indianapolis, Ind.). Gene expression was calculated relative to GAPDH (for APC) or 5S rRNA (for miR-135a) using the comparative cycle time ($C_t$) method.

Quantitative Real-Time PCR (qRT-PCR)

Total cellular RNA was extracted using Trizol™ reagent (Invitrogen™). In order to quantify APC mRNA expression levels, cDNA was synthesized using the iScript™ cDNA synthesis kit (Bio-Rad™ Laboratories, Richmond, Va., USA) and qRT-PCR was carried out using iQ™ SYBR Green master mix (Bio-Rad™). Primer sequences used are: APC, 50-GGAAGCAGAGAGAAAGTACTGGA-30 (sense, SEQ ID NO: 1) and 50-CTGAAGTTGAGCG-TAATACCAG-30 (antisense, SEQ ID NO: 2), GAPDH, 50-GTATTGGGCGCCTGGTCACC-30 (sense, SEQ ID NO: 3) and 50-CGGGAAGATG GTGATGG-30 (antisense, SEQ ID NO: 4). Expression of miR-135a and 5S sRNA as a reference was analyzed by the mirVana™ qRT-PCR miRNA Detection Kit (Ambion™/Applied Biosystems™, Austin, Tex., USA), in conjunction with RT-PCR with SYBR Green™ I (Bio-Rad™). All reactions were conducted in triplicate in a LightCycler™ 480 Real-Time PCR System (Roche™, Indianapolis, Ind., USA). Gene expression was calculated relative to GAPDH (for APC) or 5S rRNA (for miR-135a) using the comparative cycle time (Ct) method.

Transfections and Luciferase Assay

Double-stranded RNA oligos representing a mature sequence that mimics endogenous miR-135a, anti-miR-135a designed to inhibit endogenous miR-135a, and anti-miR negative control were all obtained from Ambion™ and were transfected into cell lines at ~50% confluence at 30 nM concentration with siLentFect (Bio-Rad™). For luciferase activity analysis, cells were seeded in 96-well plates and 100 ng Luc-APC-3'UTR reporter vector (SwitchGear Genomics™, Menlo Park, Calif.) and 30 nM miR-135a mimic or 30 nM non-targeting control were cotransfected with Lipofectamine™ 2000 (Invitrogen™). An empty vector, containing random genomic fragments served as a negative control. The next day, luciferase activity was measured using the Dual-Glo® Luciferase assay system (Promega™, Madison, Wis.). For siRNA-mediated APC knockdown, a siRNA against human APC and a scramble non-targeting siRNA (ON-Target PLUS Smartpool™, Dharmacon™) were transfected with Dharmacon™ Transfection reagent I into A549 cells before analyzing for protein expression at 48 hr post-transfection. For the paclitaxel dose response, cells were re-seeded 24 h after transfection and treated with paclitaxel the next day and harvested 48 hr post-treatment using MTT assay.

Annexin V Assay

Annexin V/7-amino-actinomycin D labeling was performed according to the manufacturer's instructions (BD Pharmingen™, San Diego, Calif., USA, 559 763) and samples were analyzed by flow cytometry. Briefly, cells were treated for 48-72 h with either vehicle or 100 nM paclitaxel. Cells were trypsinized and washed with phosphate-buffered saline before resuspending in assay binding buffer. Annexin V and 7-amino-actinomycin labeling was performed at room temperature for 15 min before analysis by flow cytometry (BD FACScan™, San Jose, Calif., USA).

Western Blot and Immunocytochemical Studies

Protein was extracted and the protein content was determined with Bio-Rad Protein Assay Kit (Bio-Rad) using bovine serum albumin as the standard. Protein samples (50 μg) were fractionated by SDS-PAGE (7% polyacrylamide gels) and transferred to PVDF membrane (Millipore, Bedford, Mass.). The samples were incubated overnight at 4° C. with a primary antibody directed against the C-terminus of APC (Santa Cruz Biotechnology, Santa Cruz, Calif.). Bound secondary HRP-conjugated antibodies were detected using the ECL detection system (Amersham/GE Healthcare, Pittsburgh, Pa.). Immunofluorescence for APC was carried out on cells seeded on round glass coverslips coated with 10 μg/ml fibronectin (BD Biosciences) in 24-well plates. Prior to staining, cells were treated with 30 nM of miRNA inhibitor. At the end of treatment, cells were washed with ice-cold PBS containing 1 mM $MgCl_2$ and 1 mM $CaCl_2$. Cells were fixed with 3.7% formaldehyde (Sigma) 15 minutes at room temperature and stained for APC (1:50) with the primary antibody for 1 hr followed by extensive washing and incubation with secondary antibody (Alexa 488-conjugated donkey anti-goat IgG, 1:1000) in the dark for 30 minutes.

Statistical Analysis

Statistical evaluation for data analysis was determined by using the unpaired Student's t-test or Wilcoxon's rank sum test. All data were shown as the mean±standard error (SE). A statistical difference of $P<0.05$ was considered significant.

REFERENCES CITED IN DISCLOSURE

Anand S, Penrhyn-Lowe S, Venkitaraman A R (2003). AURORA-A amplification overrides the mitotic spindle assembly checkpoint, inducing resistance to Taxol. *Cancer Cell* 3: 51-62.

Aoki K, Taketo M M (2007). Adenomatous polyposis coli (APC): a multi-functional tumor suppressor gene. *J Cell Sci* 120: 3327-35.

Blower P E, Verducci J S, Lin S, Zhou J, Chung J H, Dai Z et al (2007). MicroRNA expression profiles for the NCI-60 cancer cell panel. *Mol Cancer Ther* 6: 1483-91.

Chu Q, Vincent M, Logan D, Mackay J A, Evans W K (2005). Taxanes as first-line therapy for advanced non-small cell lung cancer: a systematic review and practice guideline. *Lung Cancer* 50: 355-74.

Cleveland W S (1979). Robust locally weighted regression and smoothing scatter plots. *J Amer Statist Assoc* 74: 829-836.

Cochrane D R, Spoelstra N S, Howe E N, Nordeen S K, Richer J K (2009). MicroRNA-200c mitigates invasiveness and restores sensitivity to microtubule-targeting chemotherapeutic agents. *Mol Cancer Ther*.

Dikovskaya D, Schiffmann D, Newton I P, Oakley A, Kroboth K, Sansom O et al (2007). Loss of APC induces polyploidy as a result of a combination of defects in mitosis and apoptosis. *J Cell Riot* 176: 183-95.

Dombernowsky P, Gehl J, Boesgaard M, Paaske T, Jensen B V (1996). Doxorubicin and paclitaxel, a highly active combination in the treatment of metastatic breast cancer. *Semin Oncol* 23: 23-7.

Erson A E, Petty E M (2009). miRNAs and cancer: New research developments and potential clinical applications. *Cancer Biol Ther* 8: 2317-22.

Esquela-Kerscher A, Slack F J (2006). Oncomirs—microRNAs with a role in cancer. *Nat Rev Cancer* 6: 259-69.

Fodde R, Kuipers J, Rosenberg C, Smits R, Kielman M, Gaspar C et al (2001). Mutations in the APC tumour suppressor gene cause chromosomal instability. *Nat Cell Biol* 3: 433-8.

Fong G H (2008). Mechanisms of adaptive angiogenesis to tissue hypoxia. *Angiogenesis* 11: 121-40.

Fujita Y, Kojima K, Ohhashi R, Hamada N, Nozawa Y, Kitamoto A et al (2010). MiR-148a attenuates paclitaxel-resistance of hormone-refractory, drug-resistant prostate cancer PC3 cells by regulating MSK1 expression. *J Biol Chem*.

Gelfand V I, Bershadsky A D (1991). Microtubule dynamics: mechanism, regulation, and function. *Annu Rev Cell Biol* 7: 93-116.

Giles R H, van Es J H, Clevers H (2003). Caught up in a Wnt storm: Wnt signaling in cancer. *Biochim Biophys Acta* 1653: 1-24.

Goldie J H, Coldman A J (1979). A mathematic model for relating the drug sensitivity of tumors to their spontaneous mutation rate. *Cancer Treat Rep* 63: 1727-33.

Greenberger L M, Lothstein L, Williams S S, Horwitz S B (1988). Distinct P-glycoprotein precursors are overproduced in independently isolated drug-resistant cell lines. *Proc Natl Acad Sci USA* 85: 3762-6.

Haldar S, Chintapalli J, Croce C M (1996). Taxol induces bcl-2 phosphorylation and death of prostate cancer cells. *Cancer Res* 56: 1253-5.

Hoffman R M (1991). Three-dimensional histoculture: origins and applications in cancer research. *Cancer Cells* 3: 86-92.

Huang G, Chen L (2010). Recombinant human endostatin improves anti-tumor efficacy of paclitaxel by normalizing tumor vasculature in Lewis lung carcinoma. *J Cancer Res Clin Oncol*.

Iorio M V, Ferracin M, Liu C G, Veronese A, Spizzo R, Sabbioni S et al (2005). MicroRNA gene expression deregulation in human breast cancer. *Cancer Res* 65: 7065-70.

Kaplan K B, Burds A A, Swedlow J R, Bekir S S, Sorger P K, Nathke I S (2001). A role for the Adenomatous Polyposis Coli protein in chromosome segregation. *Nat Cell Biol* 3: 429-32.

Kobayashi H, Man S, Graham C H, Kapitain S J, Teicher B A, Kerbel R S (1993). Acquired multicellular-mediated resistance to alkylating agents in cancer. *Proc Natl Acad Sci USA* 90: 3294-8.

Kovalchuk O, Filkowski J, Meservy J, Ilnytskyy Y, Tryndyak V P, Chekhun V F et al (2008). Involvement of microRNA-451 in resistance of the MCF-7 breast cancer cells to chemotherapeutic drug doxorubicin. *Mol Cancer Ther* 7: 2152-9.

Lepourcelet M, Chen Y N, France D S, Wang H, Crews P, Petersen F et al (2004). Small-molecule antagonists of the oncogenic Tcf/beta-catenin protein complex. *Cancer Cell* 5: 91-102.

Lu J, Getz G, Miska E A, Alvarez-Saavedra E, Lamb J, Peck D et al (2005). MicroRNA expression profiles classify human cancers. *Nature* 435: 834-8.

Mackler N J, Pienta K J (2005). Drug insight: Use of docetaxel in prostate and urothelial cancers. *Nat Clin Pract Urol* 2: 92-100; quiz 1 p following 112.

Mahon P C, Hirota K, Semenza G L (2001). FIH-1: a novel protein that interacts with HIF-1alpha and VHL to mediate repression of HIF-1 transcriptional activity. *Genes Dev* 15: 2675-86.

McGrogan B T, Gilmartin B, Carney D N, McCann A (2008). Taxanes, microtubules and chemoresistant breast cancer. *Biochim Biophys Acta* 1785: 96-132.

Meads M B, Gatenby R A, Dalton W S (2009). Environment-mediated drug resistance: a major contributor to minimal residual disease. *Nat Rev Cancer* 9: 665-74.

Mercatelli N, Coppola V, Bonci D, Miele F, Costantini A, Guadagnoli M et al (2008). The inhibition of the highly expressed miR-221 and miR-222 impairs the growth of prostate carcinoma xenografts in mice. *PLoS ONE* 3: e4029.

Mozzetti S, Ferlini C, Concolino P, Filippetti F, Raspaglio G, Prislei S et al (2005). Class III beta-tubulin overexpression is a prominent mechanism of paclitaxel resistance in ovarian cancer patients. *Clin Cancer Res* 11: 298-305.

Nagel R, le Sage C, Diosdado B, van der Waal M, Oude Vrielink J A, Bolijn A et al (2008). Regulation of the adenomatous polyposis coli gene by the miR-135 family in colorectal cancer. *Cancer Res* 68: 5795-802.

Oguri T, Ozasa H, Uemura T, Bessho Y, Miyazaki M, Maeno K et al (2008). MRP7/ABCC10 expression is a predictive biomarker for the resistance to paclitaxel in non-small cell lung cancer. *Mol Cancer Ther* 7: 1150-5.

Okugawa K, Kobayashi H, Hirakawa T, Sonoda T, Ogura T, Nakano H (2004). In vivo establishment and characterization of a paclitaxel-resistant human ovarian cancer cell line showing enhanced growth properties and drug-resistance only in vivo. *J Cancer Res Clin Oncol* 130: 178-86.

Patel N, Chatterjee S K, Vrbanac V, Chung I, Mu C J, Olsen R R et al (2010). Rescue of paclitaxel sensitivity by repression of Prohibitin1 in drug-resistant cancer cells. *Proc Natl Acad Sci USA* 107: 2503-8.

Perkins C, Kim C N, Fang G, Bhalla K N (1998). Overexpression of Apaf-1 promotes apoptosis of untreated and paclitaxel- or etoposide-treated H L-60 cells. *Cancer Res* 58: 4561-6.

Pollard J W (2004). Tumour-educated macrophages promote tumour progression and metastasis. *Nat Rev Cancer* 4: 71-8.

Ritchie M E, Silver J, Oshlack A, Holmes M, Diyagama D, Holloway A et al (2007). A comparison of background correction methods for two-colour microarrays. *Bioinformatics* 23: 2700-7.

Rottenberg S, Nygren A O, Pajic M, van Leeuwen F W, van der Heijden I, van de Wetering K et al (2007). Selective induction of chemotherapy resistance of mammary tumors in a conditional mouse model for hereditary breast cancer. *Proc Natl Acad Sci USA* 104: 12117-22.

Schiff P B, Fant J, Horwitz S B (1979). Promotion of microtubule assembly in vitro by taxol. *Nature* 277: 665-7.

Shi J, Orth J D, Mitchison T (2008). Cell type variation in responses to antimitotic drugs that target microtubules and kinesin-5. *Cancer Res* 68: 3269-76.

Sorrentino A, Liu C G, Addario A, Peschle C, Scambia G, Ferlini C (2008). Role of microRNAs in drug-resistant ovarian cancer cells. *Gynecol Oncol* 111: 478-86.

Starling J J, Maciak R S, Hinson N A, Hoskins J, Laguzza B C, Gadski R A et al (1990). In vivo selection of human tumor cells resistant to monoclonal antibody-Vinca alkaloid immunoconjugates. *Cancer Res* 50: 7634-40.

Sudo T, Nitta M, Saya H, Ueno N T (2004). Dependence of paclitaxel sensitivity on a functional spindle assembly checkpoint. *Cancer Res* 64: 2502-8.

Takeda M, Mizokami A, Mamiya K, Li Y Q, Zhang J, Keller E T et al (2007). The establishment of two paclitaxel-resistant prostate cancer cell lines and the mechanisms of paclitaxel resistance with two cell lines. *Prostate* 67: 955-67.

Teicher B A, Herman T S, Holden S A, Wang Y Y, Pfeffer M R, Crawford J W et al (1990). Tumor resistance to alkylating agents conferred by mechanisms operative only in vivo. *Science* 247: 1457-61.

Villeneuve D J, Hembruff S L, Veitch Z, Cecchetto M, Dew W A, Parissenti A M (2006). cDNA microarray analysis of isogenic paclitaxel- and doxorubicin-resistant breast tumor cell lines reveals distinct drug-specific genetic signatures of resistance. *Breast Cancer Res Treat* 96: 17-39.

Wakelee H, Ramalingam S, Belani C P (2005). Docetaxel in advanced non-small cell lung cancer. *Expert Rev Anticancer Ther* 5: 13-24.

Xia L, Zhang D, Du R, Pan Y, Zhao L, Sun S et al (2008). miR-15b and miR-16 modulate multidrug resistance by targeting BCL2 in human gastric cancer cells. *Int J Cancer* 123: 372-9.

Xie X, Lu J, Kulbokas E J, Golub T R, Mootha V, Lindblad-Toh K et al (2005). Systematic discovery of regulatory motifs in human promoters and 3' UTRs by comparison of several mammals. *Nature* 434: 338-45.

Yang Y H, Speed T (2002). Design issues for cDNA microarray experiments. Nat Rev Genet 3: 579-88.

Zhang T, Otevrel T, Gao Z, Ehrlich S M, Fields J Z, Boman B M (2001). Evidence that APC regulates survivin expression: a possible mechanism contributing to the stem cell origin of colon cancer. *Cancer Res* 61: 8664-7.

Zhou M, Liu Z, Zhao Y, Ding Y, Liu H, Xi Y et al (2010). MicroRNA-125b confers the resistance of breast cancer cells to paclitaxel through suppression of pro-apoptotic Bcl-2 antagonist killer 1 (Bak1). *J Biol Chem*.

The invention claimed is:

1. A method for treating taxane-resistant cancer, the method comprising: administering a taxane and an inhibitor of the miR-135a to a subject having taxane-resistant cancer, thereby treating the taxane-resistant cancer.

2. The method of claim 1, wherein the inhibitor comprises an antagomir, an oligonucleotide, or a small molecule.

3. The method of claim 1, wherein the taxane is paclitaxel, cabazitaxel, or docetaxel.

4. The method of claim 1, wherein the taxane-resistant cancer comprises a prostate cancer, a breast cancer, a uterine cancer, an ovarian cancer, a lung cancer, a bladder cancer, a prostate cancer, a melanoma, a head and neck cancer or an esophageal cancer.

5. The method of claim 1, wherein the subject is human.

6. The method of claim 1, wherein the inhibitor comprises an antagomir or an oligonucleotide.

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 1
ggaagcagag agaaagtact gga                                              23

<210> SEQ ID NO 2
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 2
ctgaagttga gcgtaatacc ag                                               22

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 3
gtattgggcg cctggtcacc                                                  20

<210> SEQ ID NO 4
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 4
cgggaagatg gtgatgg                                                     17
```

7. A method of killing a taxane-resistant cancer cell, the method comprising: contacting the cell with a taxane and an inhibitor of an miR-135a, thereby killing the cell.

8. The method of claim 7, wherein the inhibitor comprises an antagomir, an oligonucleotide, or a small molecule.

9. The method of claim 7, wherein the taxane-resistant cancer cell comprises a prostate cancer cell, a breast cancer cell, a uterine cancer cell, an ovarian cancer cell, a lung cancer cell, a bladder cancer cell, a prostate cancer cell, a melanoma cell, a head and neck cancer cell or an esophageal cancer cell.

10. The method of claim 7, wherein the taxane-resistant cell is human.

11. The method of claim 7, wherein the inhibitor comprises an antagomir or an oligonucleotide.

12. A method comprising: administering an effective therapeutic amount of a taxane and a therapeutically effective amount of an inhibitor of the miR-135a pathway to a subject for treatment of a taxane-resistant cancer, wherein the subject was first determined to have a taxane-resistant cancer.

13. The method of claim 12, wherein the subject is presently receiving treatment with a taxane or was previously treated with a taxane.

14. The method of claim 12, wherein the subject was first determined to have a taxane-resistant cancer by comparing the level of miR-135a in a biological sample obtained from the subject to a reference sample, wherein an increase in the level of miR-135a relative to the reference sample indicates that the subject has a taxane-resistant cancer and wherein no change or a decrease in the level of miR-135a relative to the reference sample indicates that the subject has a cancer that is not taxane-resistant.

* * * * *

UNITED STATES PATENT AND TRADEMARK OFFICE
CERTIFICATE OF CORRECTION

PATENT NO. : 9,687,467 B2
APPLICATION NO. : 14/009686
DATED : June 27, 2017
INVENTOR(S) : Bruce R. Zetter et al.

It is certified that error appears in the above-identified patent and that said Letters Patent is hereby corrected as shown below:

On the Title Page

Item (57) Lines 4 and 9 of the Abstract, two instances, "miR-135*a*" should read --miR-135a--.

In the Claims

At Column 46, Line 4, Claim 1, "of the miR-135a" should read --of miR-135a--.

At Column 47, Line 3, Claim 7, "of an miR-135a" should read --of miR-135a--.

At Column 48, Line 1, Claim 12, "of the miR-135a pathway to a" should read --of miR-135a to a--.

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*

UNITED STATES PATENT AND TRADEMARK OFFICE
CERTIFICATE OF CORRECTION

PATENT NO. : 9,687,467 B2
APPLICATION NO. : 14/009686
DATED : June 27, 2017
INVENTOR(S) : Bruce R. Zetter et al.

Page 1 of 1

It is certified that error appears in the above-identified patent and that said Letters Patent is hereby corrected as shown below:

In the Specification

At Column 1, Line 16, please replace the paragraph titled GOVERNMENT SUPPORT with the following paragraph:
GOVERNMENT LICENSE RIGHTS
This invention was made with government support under grant number CA037393 awarded by The National Institutes of Health. The government has certain rights in the invention.

Signed and Sealed this
Seventeenth Day of March, 2020

Andrei Iancu
*Director of the United States Patent and Trademark Office*